US 6,622,730 B2

(12) United States Patent
Ekvall et al.

(10) Patent No.: US 6,622,730 B2
(45) Date of Patent: Sep. 23, 2003

(54) DEVICE FOR MARKING AND ALIGNING POSITIONS ON THE HEART

(75) Inventors: Craig A. Ekvall, Elk River, MN (US); Robert M. Vidlund, Maplewood, MN (US); Todd J. Mortier, Minneapolis, MN (US); Jeffrey P. LaPlante, Minneapolis, MN (US); Edward J. Matthees, Minneapolis, MN (US); Julie M. Bulver, Plymouth, MN (US)

(73) Assignee: Myocor, Inc., Maple Grove, MN (US)

( * ) Notice: Subject to any disclaimer, the term of this patent is extended or adjusted under 35 U.S.C. 154(b) by 231 days.

(21) Appl. No.: 09/821,756

(22) Filed: Mar. 30, 2001

(65) Prior Publication Data

US 2002/0139377 A1 Oct. 3, 2002

(51) Int. Cl.[7] .............................................. A61B 19/00
(52) U.S. Cl. .......................... 128/898; 600/16; 128/897
(58) Field of Search ...................... 128/897, 898, 128/899; 600/16, 37; 606/1; 607/153; 623/2.1, 3.1

(56) References Cited

U.S. PATENT DOCUMENTS

| | | | |
|---|---|---|---|
| 4,192,293 A | 3/1980 | Asrican | 128/1 D |
| 4,261,342 A | 4/1981 | Aranguren Duo | 128/1 R |
| 4,372,293 A | 2/1983 | Vijil-Rosales | 128/1 R |
| 4,409,974 A | 10/1983 | Freedland | 128/92 B |
| 4,536,893 A | 8/1985 | Parravicini | 623/3 |
| 4,690,134 A | 9/1987 | Snyders | 128/64 |
| 4,705,040 A | 11/1987 | Mueller et al. | 128/334 |
| 4,936,857 A | 6/1990 | Kulik | 623/3 |
| 4,944,753 A | 7/1990 | Burgess et al. | 623/16 |
| 4,960,424 A | 10/1990 | Grooters | 623/2 |
| 4,997,431 A | 3/1991 | Isner et al. | 606/15 |
| 5,106,386 A | 4/1992 | Isner et al. | 606/15 |
| 5,131,905 A | 7/1992 | Grooters | 600/16 |

(List continued on next page.)

FOREIGN PATENT DOCUMENTS

| | | |
|---|---|---|
| DE | 36 14 292 | 11/1987 |
| DE | 42 34 127 | 5/1994 |
| DE | 296 19 294 | 7/1997 |
| DE | 199 47 885 | 10/1999 |
| EP | 0 583 012 | 2/1994 |
| WO | 91/19465 | 12/1991 |
| WO | 95/06447 | 3/1995 |

(List continued on next page.)

OTHER PUBLICATIONS

Batista, M.D. et al., "Partial Left Ventriculectomy to Treat End–Stage Heart Disease," *The Society of Thoracic Surgeons*, 1997, pp. 634–638.
Melvin, "Ventricular Radius–Reduction Without Resection, A Computational Assessment," 4 pages, undated.
Melvin et al., "Reduction of Ventricular Wall Tensile Stress by Geometric Remodeling Device," 1999, 6 pages.

(List continued on next page.)

*Primary Examiner*—Thor Campbell
(74) *Attorney, Agent, or Firm*—Finnegan, Henderson, Farabow, Garrett & Dunner L.L.P.

(57) ABSTRACT

According to the present invention, an alignment device for marking and aligning selected positions on a heart's surface is provided. The device includes a handle assembly having upper and lower handle portions which are detachable from one another. Each handle portion is connected to a tissue engaging member which may be secured to the surface of the heart via a vacuum. The tissue engaging members are articulatable with respect to the handle portions, such that movement of the handle portions after the tissue engaging members are secured to the heart's surface will not dislodge or displace the tissue engaging members. The tissue engaging members may be permanently or detachably connected to the handle portions. The tissue engaging members may also be used to locate and mark desired positions on the heart. In use, after the tissue engaging members are secured to the surface of the heart, the handle portions are manipulated to connect to one another.

8 Claims, 15 Drawing Sheets

U.S. PATENT DOCUMENTS

| | | | |
|---|---|---|---|
| RE34,021 E | 8/1992 | Mueller et al. ............... | 604/51 |
| 5,169,381 A | 12/1992 | Snyders ....................... | 600/16 |
| 5,192,314 A | 3/1993 | Daskalakis .................... | 623/3 |
| 5,250,049 A | 10/1993 | Michael ........................ | 606/72 |
| 5,284,488 A | 2/1994 | Sideris ....................... | 606/213 |
| 5,385,528 A | 1/1995 | Wilk ........................... | 600/18 |
| 5,433,727 A | 7/1995 | Sideris ....................... | 606/213 |
| 5,450,860 A | 9/1995 | O'Connor ................... | 128/898 |
| 5,452,733 A | 9/1995 | Sterman et al. ............ | 128/898 |
| 5,458,574 A | 10/1995 | Machold et al. ............ | 604/101 |
| 5,496,305 A | 3/1996 | Kittrell et al. ............... | 606/15 |
| 5,509,428 A | 4/1996 | Dunlop ...................... | 128/898 |
| 5,533,958 A | 7/1996 | Wilk ........................... | 600/18 |
| 5,571,215 A | 11/1996 | Sterman et al. ............... | 623/66 |
| 5,584,803 A | 12/1996 | Stevens et al. ............... | 604/4 |
| 5,593,424 A | 1/1997 | Northrup III ............... | 606/232 |
| 5,665,092 A | 9/1997 | Mangiardi et al. ........... | 606/86 |
| 5,682,906 A | 11/1997 | Sterman et al. ............ | 128/898 |
| 5,702,343 A | 12/1997 | Alferness ..................... | 600/37 |
| 5,718,725 A | 2/1998 | Sterman et al. ............... | 623/2 |
| 5,758,663 A | 6/1998 | Wilk et al. .................. | 128/898 |
| 5,800,334 A | 9/1998 | Wilk ........................... | 600/18 |
| 5,800,528 A | 9/1998 | Lederman et al. ............ | 623/3 |
| 5,814,097 A | 9/1998 | Sterman et al. ............... | 623/2 |
| 5,849,005 A | 12/1998 | Garrison et al. ............... | 606/1 |
| 5,855,614 A | 1/1999 | Stevens et al. ............... | 623/11 |
| 5,865,791 A | 2/1999 | Whayne et al. ............... | 604/49 |
| 5,902,229 A | 5/1999 | Tsitlik et al. ................. | 600/46 |
| 5,957,977 A | 9/1999 | Melvin ......................... | 623/3 |
| 5,961,440 A | 10/1999 | Schweich, Jr. et al. ....... | 600/16 |
| 5,971,910 A | 10/1999 | Tsitlik et al. ................. | 600/16 |
| 5,971,911 A | 10/1999 | Wilk ........................... | 600/18 |
| 5,972,022 A | 10/1999 | Huxel ......................... | 606/215 |
| 5,984,857 A | 11/1999 | Buck et al. ................... | 600/16 |
| 6,024,096 A | 2/2000 | Buckberg .................... | 128/898 |
| 6,024,756 A | 2/2000 | Huebsch et al. ............. | 606/213 |
| 6,045,497 A | 4/2000 | Schweich, Jr. et al. ....... | 600/16 |
| 6,050,936 A | 4/2000 | Schweich, Jr. et al. ....... | 600/37 |
| 6,059,715 A | 5/2000 | Schweich, Jr. et al. ....... | 600/16 |
| 6,071,303 A | 6/2000 | Laufer ......................... | 607/96 |
| 6,077,214 A | 6/2000 | Mortier et al. ................ | 600/16 |
| 6,077,218 A | 6/2000 | Alferness ..................... | 600/37 |
| 6,079,414 A | 6/2000 | Roth ........................... | 128/898 |
| 6,085,754 A | 7/2000 | Alferness et al. ............ | 128/898 |
| 6,095,968 A | 8/2000 | Snyders ....................... | 600/16 |
| 6,110,100 A | 8/2000 | Talpade ....................... | 600/37 |
| 6,117,159 A | 9/2000 | Huebsch et al. ............. | 606/213 |
| 6,123,662 A | 9/2000 | Alferness et al. ............ | 600/37 |
| 6,125,852 A | 10/2000 | Stevens et al. ............... | 128/898 |
| 6,126,590 A | 10/2000 | Alferness ..................... | 600/37 |
| 6,155,968 A | 12/2000 | Wilk ........................... | 600/16 |
| 6,155,972 A | 12/2000 | Nauertz et al. ............... | 600/37 |
| 6,162,168 A | 12/2000 | Schweich, Jr. et al. ....... | 600/16 |
| 6,165,119 A | 12/2000 | Schweich, Jr. et al. ....... | 600/16 |
| 6,165,120 A | 12/2000 | Schweich, Jr. et al. ....... | 600/16 |
| 6,165,121 A | 12/2000 | Alferness ..................... | 600/37 |
| 6,165,122 A | 12/2000 | Alferness ..................... | 600/37 |
| 6,169,922 B1 | 1/2001 | Alferness et al. ............. | 607/5 |
| 6,174,279 B1 | 1/2001 | Girard ......................... | 600/37 |
| 6,179,791 B1 | 1/2001 | Krueger ....................... | 600/587 |
| 6,190,408 B1 | 2/2001 | Melvin ....................... | 623/3.1 |
| 6,193,648 B1 | 2/2001 | Krueger ....................... | 600/37 |
| 6,221,103 B1 | 4/2001 | Melvin ....................... | 623/3.1 |
| 6,221,104 B1 | 4/2001 | Buckberg et al. ............ | 623/3.1 |
| 6,224,540 B1 | 5/2001 | Lederman et al. ............ | 600/37 |
| 6,230,714 B1 | 5/2001 | Alferness et al. ........... | 128/898 |
| 6,238,334 B1 | 5/2001 | Easterbrook, III et al. .... | 600/16 |
| 6,241,654 B1 | 6/2001 | Alferness ..................... | 600/37 |
| 6,258,021 B1 | 7/2001 | Wilk ........................... | 600/16 |

FOREIGN PATENT DOCUMENTS

| | | |
|---|---|---|
| WO | 95/16476 | 6/1995 |
| WO | 96/04852 | 2/1996 |
| WO | 96/40356 | 12/1996 |
| WO | 97/24101 | 7/1997 |
| WO | 98/03213 | 1/1998 |
| WO | 98/14136 | 4/1998 |
| WO | 98/18393 | 5/1998 |
| WO | 98/26738 | 6/1998 |
| WO | 98/29041 | 7/1998 |
| WO | 98/32382 | 7/1998 |
| WO | 99/11201 | 3/1999 |
| WO | 99/13777 | 3/1999 |
| WO | 99/30647 | 6/1999 |
| WO | 99/44534 | 9/1999 |
| WO | 99/44680 | 9/1999 |
| WO | 99/52470 | 10/1999 |
| WO | 99/56655 | 11/1999 |
| WO | 00/02500 | 1/2000 |
| WO | 00/06026 | 2/2000 |
| WO | 00/06028 | 2/2000 |
| WO | 00/13722 | 3/2000 |
| WO | 00/18320 | 4/2000 |
| WO | 00/27304 | 5/2000 |
| WO | 00/28912 | 5/2000 |
| WO | 00/28918 | 5/2000 |
| WO | 00/36995 | 6/2000 |
| WO | 00/42919 | 7/2000 |
| WO | 00/45735 | 8/2000 |
| WO | 00/61033 | 10/2000 |
| WO | 00/62727 | 10/2000 |
| WO | 01/03608 | 1/2001 |
| WO | 01/21070 | 3/2001 |
| WO | 01/21098 | 3/2001 |
| WO | 01/21099 | 3/2001 |
| WO | 01/50981 | 7/2001 |

OTHER PUBLICATIONS

Carpentier et al., "Myocardial Substitution with a Stimulated Skeletal Muscle: First Successful Clinical Case," Letter to the Editor, p. 1267, Sep. 25, 1996.

Ianuzzo, Ph.D., et al., "Preservation of the Latissimus Dorsi Muscle During Cardiomyoplasty Surgery," *J. Card. Surg.*, 1996:11:99–108.

Ianuzzo, et al., "On Preconditioning of Skeletal Muscle: Application to Dynamic Cardiomyoplasty," Invited Commentary, *J. Card. Surg.*, 1996:11:109–110.

Chachques, MD, et al., "Latissimus Dorsi Dynamic Cardiomyoplasty," *Ann. Thorac, Surg.*, 1989:47:600–604.

Moreira et al., "Latissimus Dorsi Cardiomyoplasty in the Treatment of Patients with Dilated Cardiomyopathy," Supplement IV Circulation, Sep. 25, 1996, 7 pages.

Lucas, et al., "Long–Term Follow–Up (12 to 35 Weeks) After Dynamic Cardiomyoplasty," *JACC*, vol. 22, No. 3, Sep. 1993:758–67.

Batista et al., "Partial Left Ventriculectomy to Improve Left Ventricular Function in End–Stage Heart Disease," *J. Card. Surg.*, 1996:11:96–98.

"Congestive Heart Failure in the United States: A New Epidemic" Data Fact Sheet, National Heart, Lung, and Blood Institute, National Institutes of Health, Dec. 9, 1996, pp. 1–6.

Kormos et al., "Experience with Univentricular Support in Mortally Ill Cardiac Transplant Candidates," *Ann. Thorac. Surg.*, 1990:49:261–71.

Wampler et al., Treatment of Cardiogenic Shock with the Hemopump Left Ventricular Assist Device, *Ann. Thorac. Surg.*, 1991:52:506–13.

McCarthy et al., "Clinical Experience with the Novacor Ventricular Assist System," *J. Thorac Cardiovasc. Surg.*, 1991:102–578–87.

Burnett et al., "Improved Survival After Hemopump Insertion in Patients Experiencing Postcardiotomy Cardiogenic Shock During Cardiopulmonary Bypass," From the Section of Transplantation, Division of Cardiovascular Surgery, Texas Heart Institute and St. Luke's Episcopal Hospital, Houston, Texas, dated even with or prior to Jan. 2, 1997, pp. 626–628.

Phillips et al., "Hemopump Support for the Failing Heart," From the Department of Cardiovascular Medicine and Surgery, Mercy Hospital Medical Center, Des Moines, Iowa, date even with or prior to Jan. 2, 1997, pp. 629–631.

Deeb et al., "Clinical Experience with the Nimbus Pump," From the University of Michigan Medical Center Section of Thoracic Surgery and Division or Cardiology, Ann Arbor, Michigan, date even with or prior to Jan. 2, 1997, pp. 632–636.

Bearnson et al., "Development of a Prototype Magnetically Suspended Rotor Ventricular Assist Device," *ASAIO Journal*, 1996, pp. 275–280.

Sakakibara et al., "A Muscle Powered Cardiac Assist Device for Right Ventricular Support: Total Assist or Partial Assist?," *Trans. Am.Soc. Artif. Intern, Organs*, vol. XXXVI, 1990, pp. 732–375.

Medtronic, Inc., 1996 Annual Shareholders Report, 79 pages.

ABIOMED, Inc., Annual Report 1996, 32 pages.

Press Release dated Sep. 16, 1996, "ABIOMED Wins $8.5 Million Federal Contract to Qualify its Artificial Heart for Human Trials," 5 pages.

Press Release dated Sep. 26, 1996, "ABIOMED's Temporary Artificial Heart System Reaches 200 U.S. Medical Center Milestone," 1 page.

Press Release dated May 17, 1996, "ABIOMED Receives FDA Approval to Expand Indications for Use of Cardiac Assist System," 1 page.

Press Release dated Oct. 3, 1995, "ABIOMED Wins $4.35 Million Contract from the National Heart, Lung and Blood Institutes to Develep Implantable Heart Booster," 1 page.

Press Release dated Sep. 29, 1995, "ABIOMED" Wins NIH Grant to Develop Calcification–Resistant Plastic Heart Valve, 1 page.

Press Release dated Aug. 25, 1995, "ABIOMED Wins Research Grant from NIH to Develop Suturing Instrument for Abdominal Surgery," 1 page.

Press Release dated Aug. 11, 1995, "ABIOMED Receives Grant from NIH to Develop Disposable Bearingless Centrifugal Blood Pump," 1 page.

Press Release dated Jun. 9, 1995, "ABIOMED Receives Grant from National Institutes of Health to Develop a Laser Welding Technique for Tissue Repair," 1 page.

Press Release dated Apr. 27, 1995, "ABIOMED's Temporary Artificial Heart System Reaches 1,000 Patient Milestone; BVS–5000 in More Than 100 U.S. Medical Centers," 1 page.

"Reversible Cardiomyopathy," *Thoratec's Heartbeat*, vol. 10.2, Aug. 1996, 4 pages.

Tsai et al., "Surface Modifying Additives for Improved Device–Blood Compatibility," *ASAIO Journal*, 1994, pp. 619–624.

Farrar et al., "A New Skeletal Muscle Linear–Pull Energy Convertor as a Power Source for Prosthetic Support Devices," *The Journal of Heart & Lung Transplantation*, vol. 11, No. 5, Sep., 1992, pp. 341–349.

Brochure entitled "Thoratec Ventricular Assist Device System—Because Heart Patients Come in All Sizes," date even with or prior to Jan. 2, 1997, 5 pages.

Press Release dated Oct. 3, 1994, "Heartmate System Becomes First Implantable Cardiac–Assist Device to be Approved for Commercial Sale in the U.S.," 2 pages.

Bocchi et al., "Clinical Outcome after Surgical Remodeling of Left Ventricle in Candidates to Heart Transplantation with Idiopathic Dilated Cardiomypathy—Short Term Results," date even with or prior or Jan. 2, 1997, 1 page.

Bach et al., "Early Improvemet in Congestive Heart Failure after Correction of Secondary Mitral Regurgitation in End–Stage Cardiomyopathy," *American Heart Journal*, Jun. 1995, pp. 1165–1170.

Schuler et al., "Temporal Response of Left Ventricular Performance to Mitral Valve Surgery," vol. 59, No. 6, Jun. 1979, pp. 1218–1231.

Huikuri, "Effect of Mitral Valve Replacement on Left Ventricular Function in Mitral Regurgitation," *Br. Heart J.*, vol. 49, 1983, pp. 328–333.

Pitarys II et al., "Long–Term Effects of Excision of the Mitral Apparatus on Global and Regional Ventricular Function in Humans," *JACC*, vol. 15, No. 3, Mar. 1, 1990, pp. 557–563.

Bolling et al., "Surgery for Acquired HEart Disease/Early Outcome of Mitral Valve Reconstruction in Patients with End–Stage Cardiomyopathy," *The Journal of Thoracic and Cardiovascular Surgery*, vol. 109, No. 4, Apr. 1995, pp. 676–683.

Masahiro Oe et al., "Surgery for Acquired Heart Disease/ Effects of Preserving Mitral Apparatus on Ventricular Systolic Function in Mitral Valve Operations in Dogs," *The Journal of Thoracic and Cardiovascular Surgery*, vol. 106, No. 6, Dec. 1993, pp. 1138–1146.

Dickstein et al., "Heart Reduction Surgery: An Analysis of the Impact on Cardiac Function," *The Journal of Thoracic and Cardiovascular Surgery*, vol. 113, No. 6, Jun. 1997, 9 pages.

McCarthy et al., "Early Results with Partial Left Ventriculectomy," From the Departments of Thoracic and Cardiovascular Surgery, Cardiology, and Transplant Center, Cleveland Clinic Foundation, Presented at the 77th Annual Meeting of the American Association of Thoracic Surgeons, May 1997, 33 pages.

Alonso–Lej, M.D., "Adjustable Annuloplasty for Tricuspid Insufficiency," *The Annals of Thoracic Surgery*, vol. 46, No. 3, Sep. 1988, 2 pages.

Kurlansky et al., "Adjustable Annuloplasty for Tricuspid Insufficiency," *Ann. Thorac. Surg.*, 44:404–406, Oct. 1987.

Boyd et al., "Tricuspid Annuloplasty," *The Journal of Thoracic Cardiovascular Surgery*, vol. 68, No. 3, Sep. 1974, 8 pages.

Melvin, "Ventricular Radius Reduction Without Resection: A Computational Analysis," *ASAIO Journal*, 45:160–165, 1999.

Edie, M.D. et al., "Surgical repair of single ventricle," *The Journal of Thoracic and Cardiovascular Surgery*, vol. 66, No. 3, Sep., 1973, pp. 350–360.

McGoon, M.D. et al., "Correction of the univentricular heart having two atrioventricular valves," *The Journal of Thoracic and Cardiovascular Surgery*, vol. 74, No. 2, Aug., 1977, pp. 218–226.

Lev, M.D., et al., "Single (Primitive) Ventricle," *Circulation*, vol. 39, May, 1969, pp. 577–591.

Westaby with Bosher, "Landmarks in Cardiac Surgery," 1977, pp. 198–199.

Shumacker, "Cardiac Aneurysms," *The Evolution of Cardiac Surgery*, 1992, pp. 159–165.

Feldt, M.D., "Current status of the septation procedure for univentricular heart," *The Journal of Thoracic and Cardiovascular Surgery*, vol. 82, No. 1, Jul. 1981, pp. 93–97.

Doty, M.D., "Septation fo the univentricular heart," *The Journal of Thoracic and Cardiovascular Surgery*, vol. 78, No. 3, Sep., 1979, pp. 423–430.

Savage, M.D., "Repair of left ventricular aneurysm," *The Journal of Thoracic and Cardiovascular Surgery*, vol. 104, No. 3, Sep., 1992, pp. 752–762.

Cox, "Left Ventricular Aneurysms: Pathophysiologic Observations and Standard Resection," *Seminars in Thoracic and Cardiovascular Surgery*, vol. 9, No. 2, Apr., 1997, pp. 113–122.

"Heart 'jacket' could help stop heart failure progression," *Clinica*, 916, Jul. 10, 2000.

McCarthy et al., "Device Based Left Ventricular Shape Change Immediately Reduces Left Ventricular Volume and Increases Ejection Fraction in a Pacing Induced Cardiomyopathy Model in Dogs: A Pilot Study," *JACC*, Feb. 2000.

Acorn Cardiovascular, Inc. Abstracts for presentation at Nov. 2000 American Heart Association meeting, 6 page.

"Nation's First 'Heart Jacket' Surgery to Treat Heart Failure Performed at HUP; Novel Cardiac Support Device' Comes to Americal After Promising Results in Europe," Jun. 26, 2000, 3 pages.

Acorn Cardiovascular Company Overview, Jun. 2000, 6 pages.

Acorn Cardiovascular Company Overview, undated, 2 pages.

Acorn Cardiovascular Executive Summary, May 2000, 7 pages.

Acorn Cardiovascular Highlights, Abstracts, Mar. 10, 1999.

Acorn Cardiovascular Highlights, Abstracts, Apr. 19, 1999.

Acorn Cardiovascular Highlights, Abstracts, Oct. 1, 1999.

Acorn Cardiovascular Highlights, Abstracts, Nov. 9, 1999.

McCarthy, Transcription of Mar. 13, 2000 Presentation by Patrick McCarthy at the American College of Cardiology.

Acorn Cardiovascular Summary, undated.

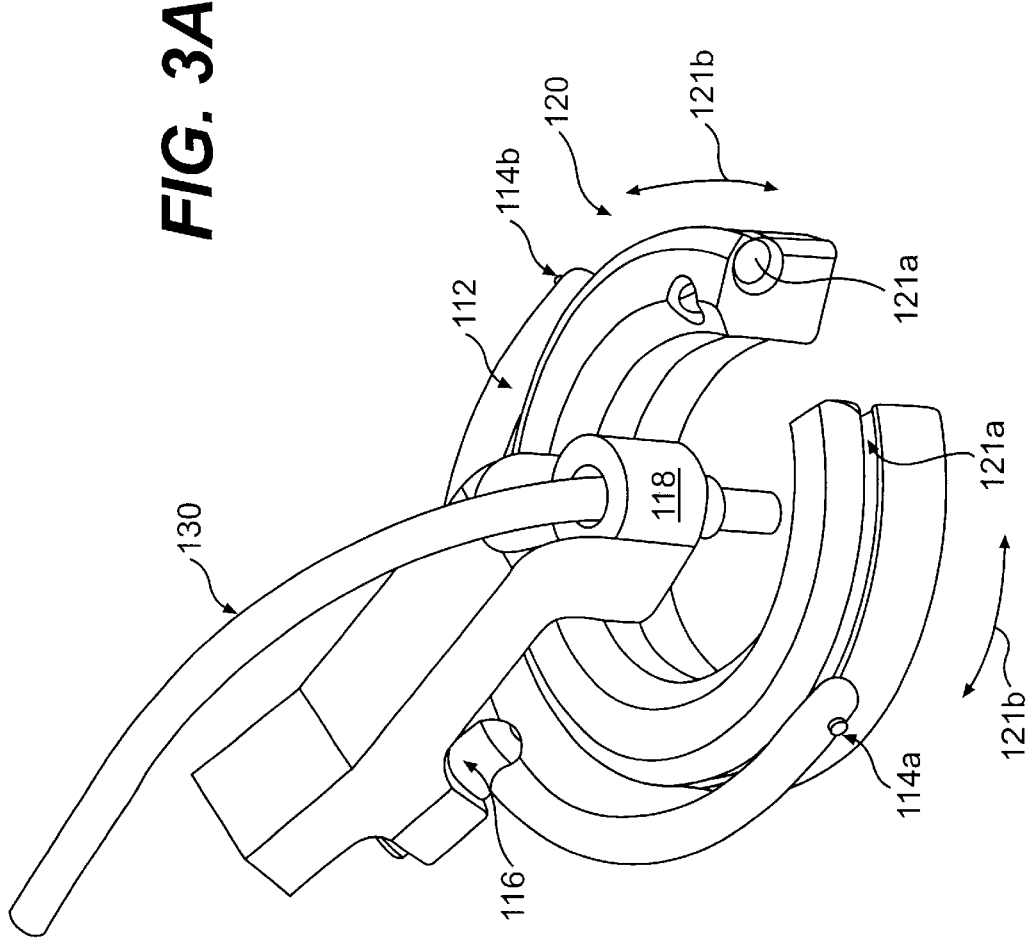

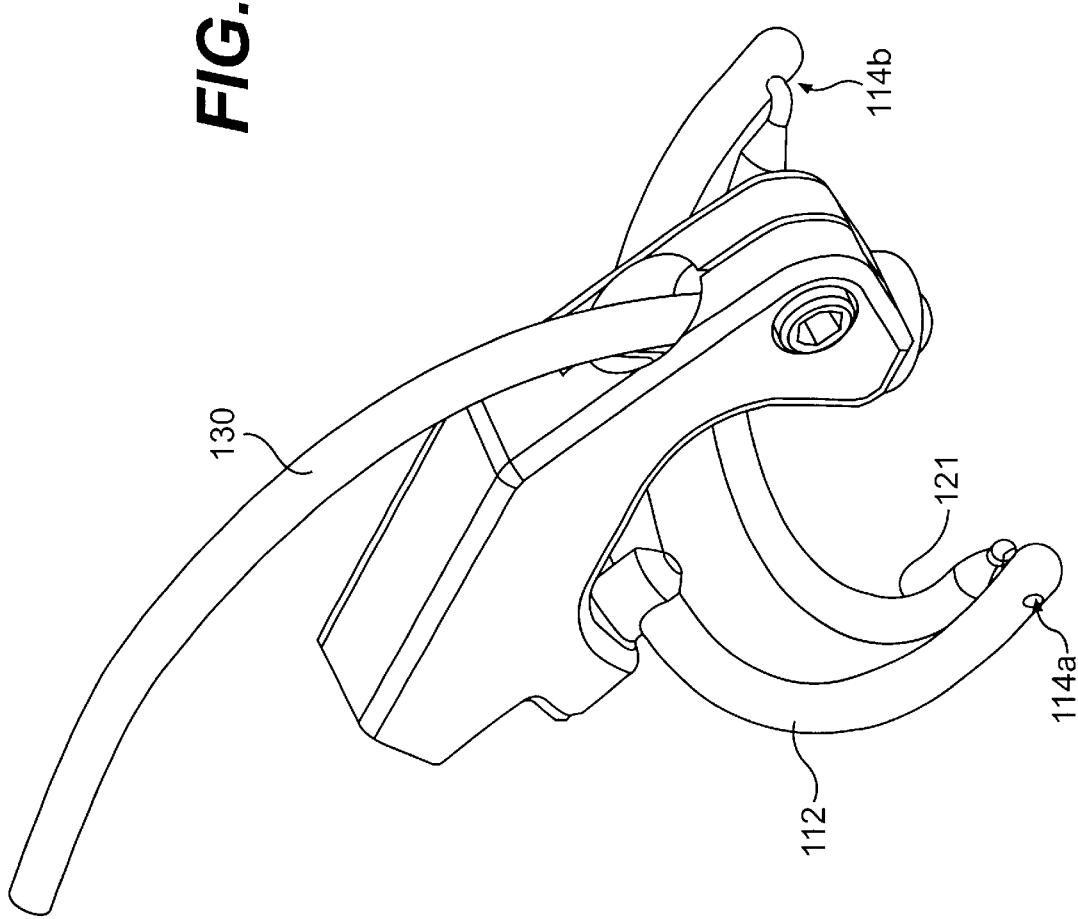

DEVICE FOR MARKING AND ALIGNING POSITIONS ON THE HEART

FIELD OF THE INVENTION

The present invention relates to a device for marking and aligning positions on a heart for receiving a device for treating the heart. In particular, the device and a method of using the device are directed toward locating and marking positions on the heart and securing the device to the heart to guide placement of a device for reducing stress on the heart.

BACKGROUND OF THE INVENTION

Heart failure is a common outcome in the progression of many forms of heart disease. Heart failure may be considered as the condition in which an abnormality of cardiac function is responsible for the inability of the heart to pump blood at a rate commensurate with the requirements of the metabolizing tissues, or can do so only at an abnormally elevated filling pressure. There are many specific disease processes that can lead to heart failure. Typically these processes result in dilatation of the left ventricular chamber. Etiologies that can lead to this form of failure include idiopathic, valvular, viral, and ischemic cardiomyopathies.

The process of ventricular dilatation is generally the result of chronic volume overload or specific damage to the myocardium. In a normal heart that is exposed to long term increased cardiac output requirements, for example, that of an athlete, there is an adaptive process of slight ventricular dilation and muscle myocyte hypertrophy. In this way, the heart fully compensates for the increased cardiac output requirements. With damage to the myocardium or chronic volume overload, however, there are increased requirements put on the contracting myocardium to such a level that this compensated state is never achieved and the heart continues to dilate.

One problem with a large dilated left ventricle is that there is a significant increase in wall tension and/or stress both during diastolic filling and during systolic contraction. In a normal heart, the adaptation of muscle hypertrophy (thickening) and ventricular dilatation maintain a fairly constant wall tension for systolic contraction. However, in a failing heart, the ongoing dilatation is greater than the hypertrophy and the result is a rising wall tension requirement for systolic contraction. This is felt to be an ongoing insult to the muscle myocyte resulting in further muscle damage. The increase in wall stress also occurs during diastolic filling. Additionally, because of the lack of cardiac output, a rise in ventricular filling pressure generally results from several physiologic mechanisms. Moreover, in diastole there is both a diameter increase and a pressure increase over normal, both contributing to higher wall stress levels. The increase in diastolic wall stress is felt to be the primary contributor to ongoing dilatation of the chamber.

Another form of heart failure results from the formation of one or more zones of ischemia, or infarction, of the myocardium. Infarction occurs when blood supply to the heart tissue has been obstructed resulting in a region of tissue that loses its ability to contract (referred to as infarcted tissue). The presence of infarcted tissue may lead to three conditions in the heart causing cardiac malfunction. These conditions are ventricular aneurysms (ventricular dyskinesia), non-aneurysmal ischemic or infarcted myocardium (ventricular akinesia), and mitral regurgitation.

A ventricular aneurysm is formed when the infarction weakens the heart wall to such an extent that the tissue stretches and thins, causing, for example, the left ventricular wall to expand during systole (dyskinesia) and form a bulge in the heart wall. Non-aneurysmal ischemic or infarcted myocardium (akinesia) occurs when a major coronary artery is occluded and results in infarction in the myocardial tissue, but without a bulging aneurysm. Finally, mitral regurgitation is a condition whereby blood leaks through the mitral valve due to an improper positioning of the valve structures that causes it not to close entirely. If the infarcted or aneurysmal region is located in the vicinity of the mitral valve, geometric abnormalities may cause the mitral valve to alter its normal position and dimension, and may lead to annular dilatation and the development of mitral regurgitation.

Prior treatments for heart failure associated with such dilatation fall into three general categories. The first treatment is pharmacological, for example, diuretics and ACE inhibitors. While drug therapies offer some beneficial effects, they do not stop progression of heart disease. The second treatment uses assist systems, for example, pumps. Although such mechanical assist devices may sustain the patient by performing the functions of the heart, such devices, at this point in time, are stop-gap measures at best, sustaining a patient until a transplant is available. Finally, surgical treatments also have been experimented with, including, for example, the Batista partial left ventriculectomy in which the left ventricle is surgically remodeled by removing a segment of the muscle wall. However, this is an extremely invasive procedure which reduces muscle mass of the heart.

SUMMARY OF THE INVENTION

The advantages and purpose of the invention will be set forth in part in the description which follows, and in part will be obvious from the description, or may be learned by practice of the invention. The advantages and purpose of the invention will be realized and attained by means of the elements and combinations particularly pointed out in the appended claims.

One aspect of the present invention includes an alignment device. The alignment device includes a first arm supporting a first heart engaging member, the first heart engaging member having a heart contacting surface, a second arm supporting a second heart engaging member, the second heart engaging member having a heart contacting surface, and a handle assembly having a first handle portion and a second handle portion, wherein the first handle portion supports the first arm and the second handle portion supports the second arm, the first and second handle portions being releasably connected to permit movement independent of one another.

According to another aspect of the invention, an alignment device includes a first arm supporting a first heart engaging member, the first heart engaging member having a heart contacting surface, wherein the first heart engaging member articulates with respect to the first arm, a second arm supporting a second heart engaging member, the second heart engaging member having a heart contacting surface, wherein the second heart engaging member articulates with respect to the second arm, and a handle assembly connected to the first and second arms.

According to a further aspect of the invention, an alignment device is provided. The alignment device includes a first arm supporting a first heart engaging member, the first heart engaging member having a first heart contacting surface and defining at least one suction chamber, a second arm supporting a second heart engaging member, the second heart engaging member having a second heart contacting surface and defining at least one suction chamber, and a handle assembly connected to the first and second arms.

According to yet another aspect of the invention, an alignment device includes a first arm supporting a first heart engaging member, the first heart engaging member having a first heart contacting surface, wherein the first heart engaging member articulates with respect to the first arm and the first heart engaging member defines at least one suction chamber, a second arm supporting a second heart engaging member, the second heart engaging member having a second heart contacting surface, wherein the second heart engaging member articulates with respect to the second arm and the second heart engaging member defines at least one suction chamber, and a handle assembly having first and second handle portions, wherein the first handle portion supports the first arm and the second handle portion supports the second arm, the first and second handle portions being releasably connected to permit movement independent of one another.

According to another aspect of the invention, a method of implanting an elongate member transverse a heart is provided. The method includes selecting first and second locations on the heart, placing a first heart engaging member at the first location, placing a second heart engaging member at the second location while the second heart engaging member is not connected to the first heart engaging member, passing a path-creating member through the first and second heart engaging members and through the heart, and placing an elongate member through the heart along a path created by the path creating member.

According to a further aspect of the invention, a method of marking positions on the heart is provided. The method includes placing a first heart engaging member on a surface of the heart at a first position, holding the first engaging member on the heart with suction, placing a second heart engaging member on a surface of the heart at a second position opposite the first position, and holding the second engaging member on the heart with suction.

According to another aspect of the invention, a method of aligning selected positions on the heart to receive a splint assembly is provided. The method includes placing a first heart engaging member on a first surface of the heart, the first heart engaging member connected to a first handle portion, securing the first heart engaging member to the first surface of the heart, placing a second heart engaging member on a second surface of the heart, the second heart engaging member connected to a second handle portion, securing the second heart engaging member to the second surface of the heart, and moving the first handle portion relative to the first heart engaging member to connect the first and second handle portions.

According to yet another aspect of the invention, an alignment device includes a first heart engaging member having a heart engaging surface and a first receiving portion, a first arm having an end configured to releasably attach to the first receiving portion, a second heart engaging member having a heart engaging surface and a second receiving portion, a second arm having an end configured to releasably attach to the second receiving portion, and a handle assembly connected to the first and second arms.

BRIEF DESCRIPTION OF THE DRAWINGS

The accompanying drawings, which are incorporated in and constitute a part of this specification, illustrate several embodiments of the invention and together with the description, serve to explain the principles of the invention. In the drawings.

FIG. 3A is an isometric view of the top of a first heart engaging member of the alignment device of FIG. 1;

FIG. 3B is an isometric view of the apparatus of FIG. 3A without the heart engaging member;

DESCRIPTION OF THE PREFERRED EMBODIMENTS

Figure 1:
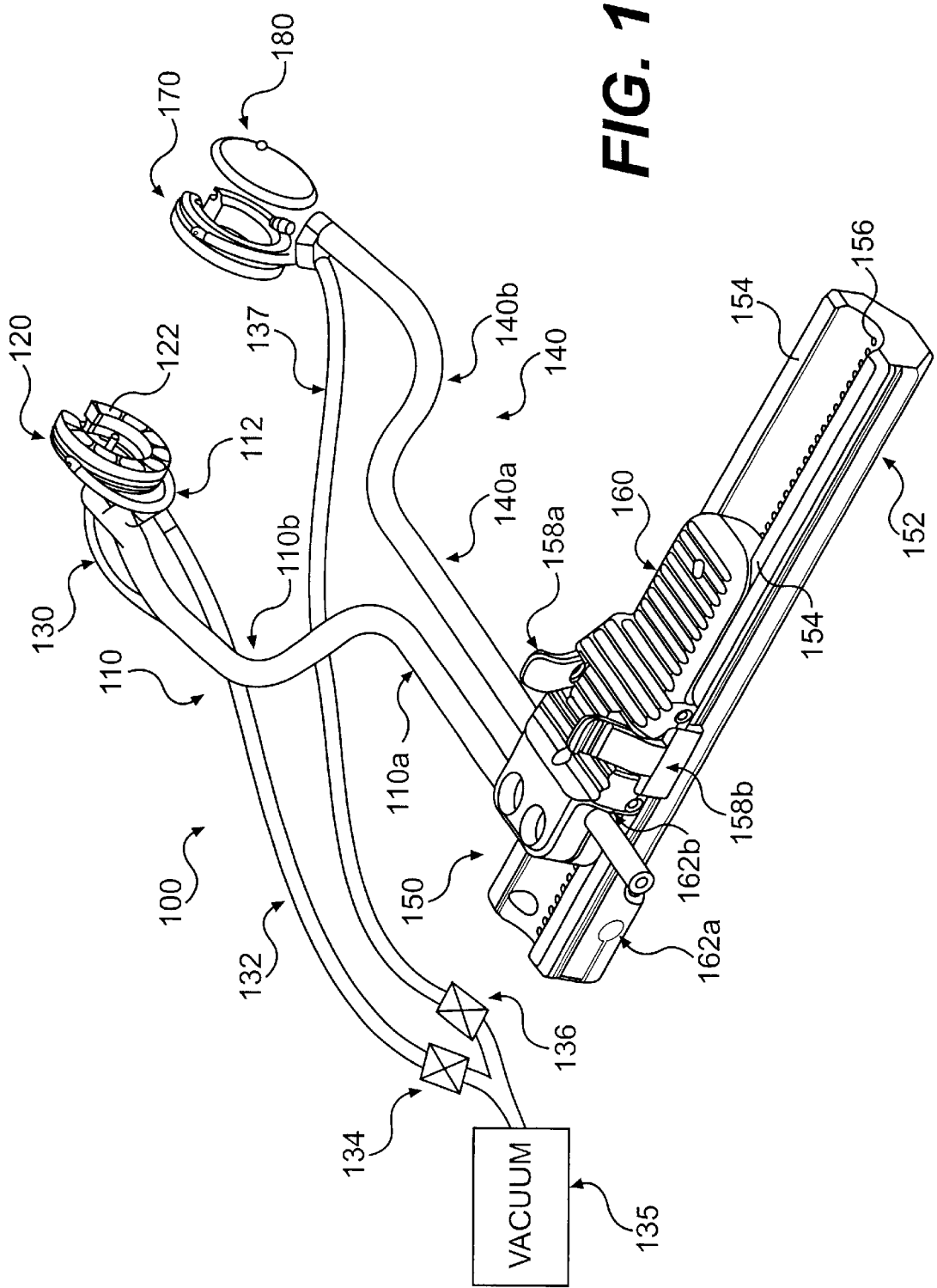
FIG. 1 is an isometric view of an alignment device according to an embodiment of the present invention.

A surgical treatment for improving cardiac function, generally referred to as geometric reshaping of the heart, is disclosed in related U.S. patent application Ser. No. 09/532,049 entitled "A Splint Assembly for Improving Cardiac Function in Hearts and Method for Implanting the Splint Assembly," and filed Mar. 21, 2000, the complete disclosure of which is incorporated herein by reference. One way of treating the heart, as discussed in the incorporated disclosure, is to place an elongate member traverse to a heart chamber, typically the left ventricle, to reduce mechanical heart wall muscle stress. Various types of elongate members can be used. Such elongate members, often called tension members or splints, for example, are preferably placed by tools used to first locate appropriate points on the heart wall for the placement of the tension member, mark the points, and align the points and guide a tension member through the heart at these points. Examples of such tools are discussed in related U.S. patent application Ser. No. 09/123,977, filed on Jul. 29, 1998, and entitled "Transventricular Implant Tools and Devices," the complete disclosure of which is incorporated herein by reference.

The tension member may be anchored at its ends external to the heart, and the amount of tension due to the length of the tension member, along with the location of the tension member and anchors, will reshape the heart chamber, and reduce a radius and cross-sectional area of that chamber. This is explained fully in the above incorporated U.S. patent application Ser. No. 09/532,049, and also in U.S. patent application Ser. No. 09/422,328 entitled "Methods and Devices for Improving Cardiac Function in Hearts," filed Oct. 21, 1999, the complete disclosure of which is incorporated by reference herein.

Models of this reshaping also can be found in U.S. Pat. No. 6,045,497, issued Apr. 4, 2000, and entitled "Heart Wall Tension Reduction Apparatus and Method," the complete disclosure of which is incorporated herein by reference. Prior to reshaping the chamber geometry, the heart walls experience high stress due to a combination of both the relatively large increased diameter of the chamber and the thinning of the chamber wall. Filling pressures and systolic pressures are typically high as well, further increasing wall stress. Geometric reshaping according to the present invention reduces the stress in the walls of the heart chamber to increase the heart's pumping efficiency, as well as to stop further dilatation of the heart.

Although the method and device are discussed below in connection with their use in the left ventricle of the heart, this method and device may be used in other chambers of the heart for similar purposes, as one of ordinary skill in the art would readily understand. The left ventricle has been selected for illustrative purposes because a large number of the disorders that the present invention treats occur in the left ventricle.

The various aspects of the invention to be discussed herein generally pertain to devices and methods for marking and aligning positions on the heart for receiving a device for treating heart conditions, preferably a transventricular splint. The inventive device and methods offer numerous advantages over the existing devices and methods of marking and aligning positions on the heart for receiving transventricular splints. The device is relatively easy to manufacture and use, and includes readily sterilizable parts. In addition, the device includes pieces which are moveable independently of one another, and which are detachable from one another, making the device simpler and easier to use. More particularly, the device includes a handle having two portions which are detachable from one another. This allows independent movement of one portion from the other portion. This is particularly useful because it allows a surgeon to work around the heart with one portion while not being limited by the other portion. This makes use of the device less cumbersome than devices in which the handle portions are not separable. Specifically, because the handle portions can be manipulated independent of one another, a first heart engaging member of the device associated with one handle portion can be positioned and attached to an area of the heart. Then, a second heart engaging member associated with the other handle portion can be positioned and attached to another area of the heart independent of the attachment of the first heart engaging member and without causing the first heart engaging member to move, as will be described further herein.

In addition, and according to another embodiment of this invention, the heart engaging members at the ends of the device are each independently articulable with respect to its corresponding handle portion. Thus, in addition to the handles being able to move independently of one another, the heart engaging members are also independently articulable, enhancing the ability of the device to maneuver with respect to the heart.

The device has other useful features, such as rounded edges on the heart engaging members to prevent trauma to the heart tissue from contact. The device is also configured to be securely attached to the heart wall without traumatizing the tissue.

This is accomplished through the use of a vacuum source supplied at a heart contacting surface of each heart engaging member. The use of suction to secure the heart engaging members to the surface of the heart reduces the chance of abrasion of the heart tissue from rough surfaces of the heart engaging members. The device can be used in conjunction with other existing devices, such as locating and marking devices, or may be used to replace such devices.

Reference will now be made in detail to the present preferred embodiments of the invention, examples of which are illustrated in the accompanying drawings. Wherever possible, the same reference numbers will be used throughout the drawings to refer to the same or like parts.

Various techniques for delivering a device, such as a transventricular splint, for treating the heart have been described in prior applications, such as U.S. patent application Ser. No. 09/123,977, filed on Jul. 29, 1998, and entitled "Transventricular Implant Tools and Devices," and U.S. patent application Ser. No. 09/532,049, filed on Mar. 21, 2000, and entitled "A Splint Assembly for Improving Cardiac Function in Hearts, and Method for Implanting the Splinting Assembly," the entire disclosures of which are incorporated herein by reference. Briefly, the delivery of a splint assembly, as described in these prior applications, may proceed in the following manner.

First, the optimal placement of a splint assembly with respect to a heart chamber should be determined. The optimal position should avoid damage to both internal cardiac structures, such as the papillary muscles, and external structures, such as blood vessels. Tools will be used to assist in the placement of splint assemblies to effectively bisect the ventricle to result in optimal radius reduction and stress reduction.

A number of possible orientations for splint placement are possible. The splint assembly, for example, may be placed across the left ventricle in a plane essentially longitudinally bisecting the ventricle. The splint assembly may extend from a location proximate to the anterior lateral papillary muscle on the ventricle free wall to a location proximate to the posterior ventricular septum. An exemplary location for the splint assembly near the anterior lateral papillary muscle is just lateral to that muscle toward the left anterior descending artery, while an exemplary location near the septum is on the posterior free wall of the right ventricle.

Any suitable number of splint assemblies to appropriately reshape the heart may be used. In one embodiment, for example, three splint assemblies may be implanted. The upper-most (basal) splint assembly may be placed in the orientation just described above. The remaining two splint assemblies may be positioned in an equidistant relationship between the basal splint assembly and the apex of the left ventricle. In this manner, the three splint assemblies essentially bisect the ventricle, producing optimal radius and stress reduction without excessive ventricular volume reduction. The positioning of the splint assemblies in this way also avoids interference with the mitral valve structure, including the chordae tendonae. Additionally, the positions described effectively avoid significant coronary arteries or veins. An additional splint assembly may be used proximate the mitral valve to improve mitral valve function, as described in U.S. patent application Ser. No. 09/680,435 entitled "Methods and Devices for the Improvement of Mitral Valve Function," filed Oct. 6, 2000, the complete disclosure of which is incorporated by reference herein.

Visualization of the internal structures of the heart, including both the papillary muscles and the septum, may occur through the use of external imaging methods, since the precise positions of internal structures may not be accurately discerned visually from the outside of the heart. An exemplary external imaging method includes the use of ultrasound probes. Ultrasound probes can either be used on the outer surface of the heart or can be positioned in the patient's esophagus (transesophageal). Such visualization methods may be used to determine where the splint assembly will be placed.

A probe/marking device may be used to both locate positions on the heart wall for splint placement and simultaneously mark and/or deliver a marker into the heart wall to mark each location. The probe/marking device may include a tip, to create a distinct, localized deflection upon contact and indentation of the heart wall visible with ultrasonic imaging. Markers may be placed once the proper positions have been identified. Examples of markers and probe/marking devices and their use are disclosed in U.S. patent application Ser. No. 09/532,049, filed on Mar. 21, 2000, and entitled "A Splint Assembly for Improving Cardiac Function in Hearts, and Method for Implanting the Splinting Assembly," the entire disclosure of which is incorporated herein by reference. As will be described, the alignment tool described below may be used in lieu of such probe/marking devices.

Once markers have been delivered to the heart wall on both sides of the chamber, an alignment device may be positioned around the heart at those locations. The alignment device may include a guide tube, through which a path-creating member, such as a needle, is first delivered at the marker locations to penetrate the heart wall. The path-creating member is extended transverse the heart such that each end of the member penetrates locations on the heart wall corresponding to the ends of the splint assembly to be implanted. The path-creating member defines a lumen extending along its length, through which a leader, attached to a tension member, may be inserted via the guide tube in the alignment device. Once the leader extends through the second marker location, the path-creating member may be removed, and the leader can be pulled which in turn pulls the tension member across the heart wall.

Next, the leader (attached to a tension member and associated pad assemblies) may be fed into a measuring and tightening device, which also is described in U.S. application Ser. No. 09/123,977, which has been incorporated by reference above. Once the tension member has been adjusted to the desired length, an anchor assembly is secured to the tension member adjacent the exterior of the heart wall. The length of the tension member extending between the pad assemblies also can be optimally determined based upon the size and condition of the patient's heart.

The present invention is directed to an improved alignment device and related methods of using that device. More particularly, an alignment device according to an embodiment of the present invention may be used to align previously located positions on the heart's surface, and to guide placement of a tension member of the splint assembly (or other device) at the aligned positions. In an alternative embodiment, the device may also be used to locate positions on the heart through which the tension member should be placed and then mark the those positions. The device, when used to locate and mark the positions, may also be used to align the positions and guide placement of a tension member of a splint assembly or other device. By performing these functions, the alignment device may be used in a method to implant a splint assembly that does not employ other locating and probe/marking devices described in disclosures incorporated above. Finally, in yet another embodiment, the device may be used in to locate and mark positions, and then guide a tension member of a splint assembly through the marked positions without aligning.

As embodied herein and shown in FIG. 1, an alignment device 100 is provided. Alignment device 100 includes a handle assembly, two arms, and two heart engaging members having heart contact surfaces.

Although described herein with respect to heart surgery, it is contemplated that alignment device 100 may be suitable for use in other surgical procedures, where a stable marking and/or alignment device is beneficial. Thus, the although the tissue engaging members of alignment device 100 have been characterized as heart engaging members, it is contemplated that they may be used to engage any type of tissue.

Figure 2:
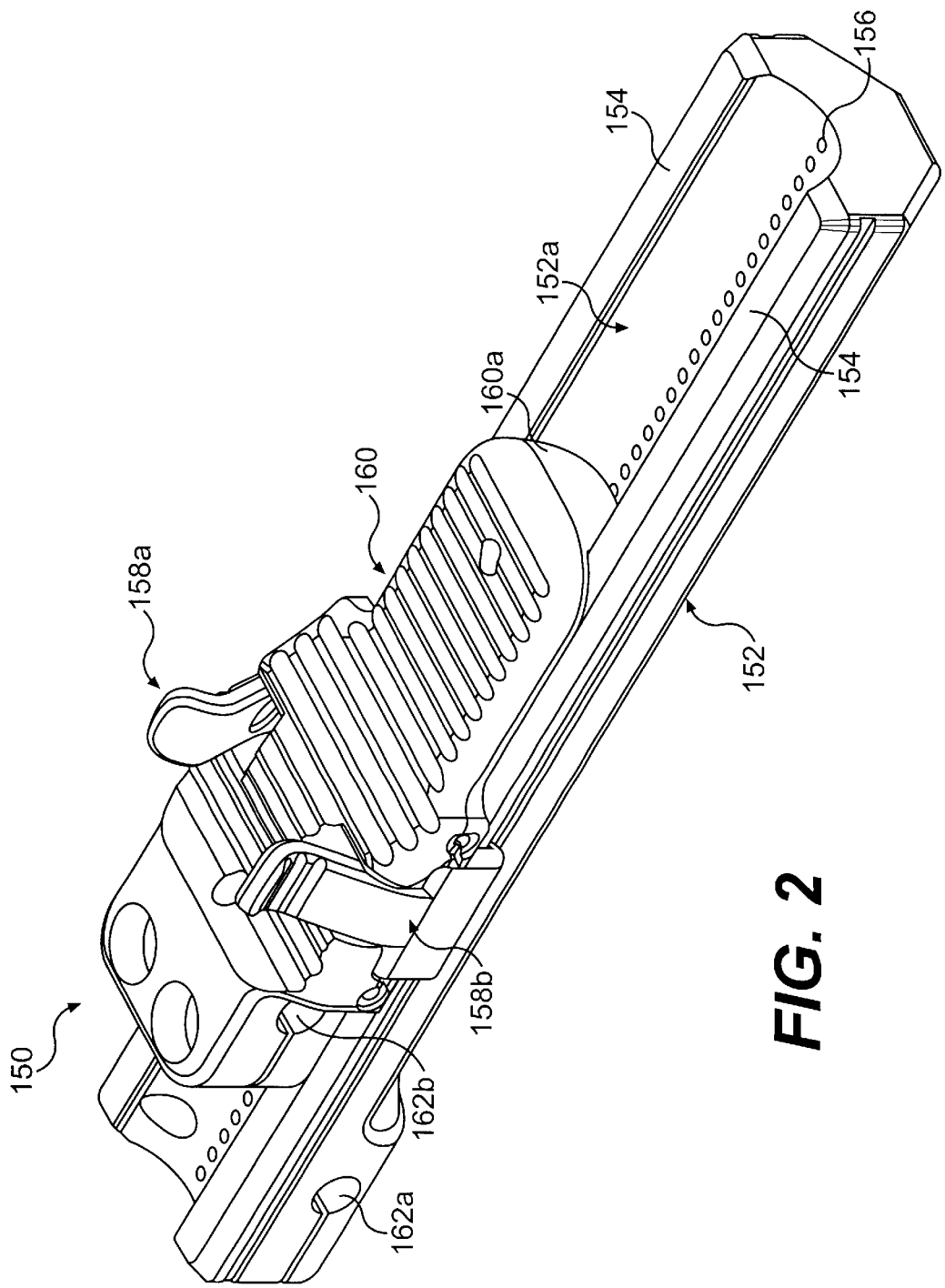
FIG. 2 is an isometric view of a handle assembly of the alignment device of FIG. 1.

As shown in FIGS. 1 and 2, a handle assembly 150 is provided. Handle assembly 150 includes a bottom handle portion 152 and an upper handle portion 160.

Bottom handle portion 152 includes rails 154 upon which the upper handle portion 160 is movable with respect to bottom handle portion 152. Bottom handle portion 152 also includes a first arm receiving aperture 162a, and upper handle portion 160 includes a second arm receiving aperture 162b. Bottom handle portion 152 also includes detents 156 to aid in controlling and limiting movement of upper handle portion 160 with respect the lower handle portion 152. Bottom handle portion 152 may be releasably connected to upper handle portion 160 by lock levers 158a, 158b. Upper handle portion 160 moves with respect to bottom handle portion 152 on spring loaded balls (not shown). The spring loaded balls are in contact with the surface of bottom handle portion 152 containing detents 156, and sit in the detents 156. Thus, for the top handle portion 160 to move with respect to the bottom handle portion 152, the spring loaded balls must move with respect to the detents 156. This is accomplished by applying a force to either one of the handle portions 152, 160 with respect to the other one of the handle portions 160, 152, respectively. When a force is applied, the springs are compressed, allowing the balls to move over the detents. Thus, the spring force applied to the balls keep the upper handle portion 160 from moving with respect to bottom handle portion 152 when such movement is not desired.

Preferably, both handle portions 152, 160 are made of a sterilizable material, such as Delrin or other suitable material, and may be made by injection molding. The bottom handle portion 152 receives the upper handle portion 160, as shown in FIG. 2, such that a part 160a of a upper handle portion sits within a trough portion 152a of lower handle portion 152. To mate upper handle portion 160 with lower handle portion 152, a the part 160a of upper handle portion 160 is pressed into the trough portion 152a of lower handle portion 152, and as part 160a is pressed into the trough portion 152a, lock levers 158a, 158b automatically open, and once part 160a of upper handle portion 160 to is in trough 152a of lower handle portion 152, the lock levers 158a, 158b "snap" into position, grasping the rails 154 of lower handle portion 152 and locking the handle portion 160 in place.

Figure 4A:
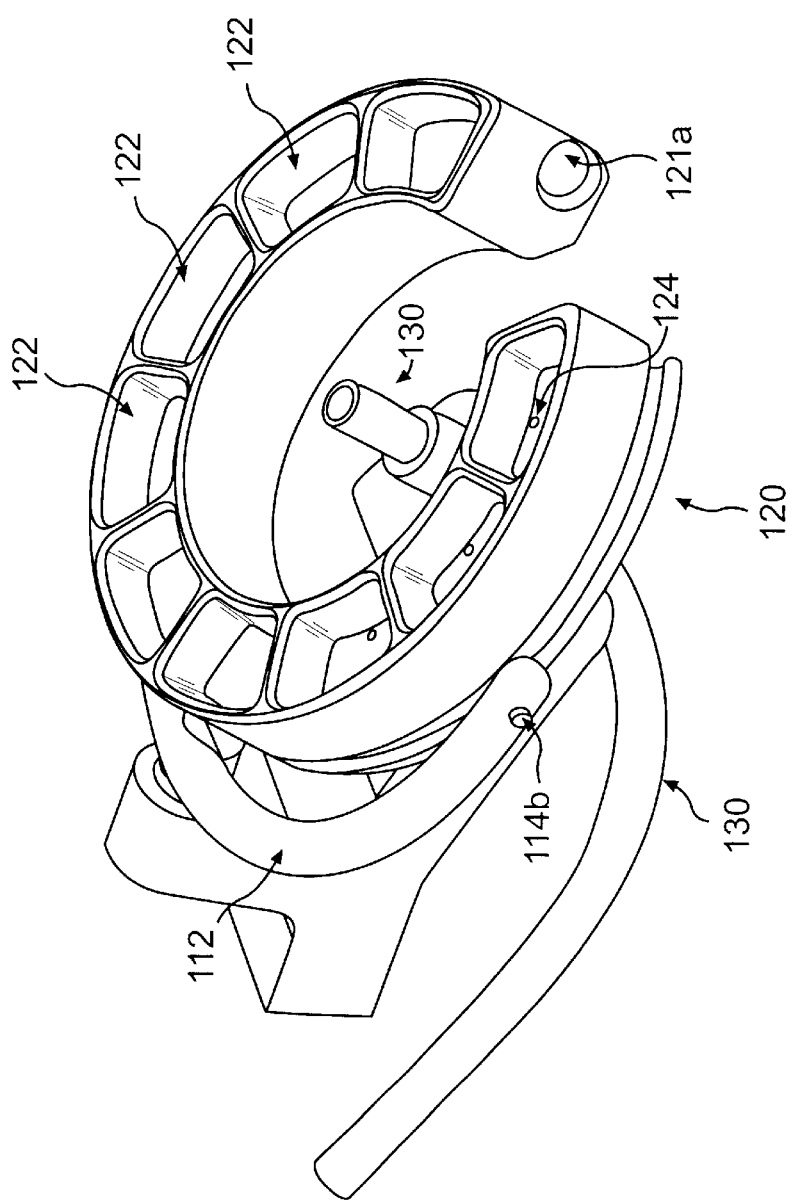
FIG. 4A is an isometric view of the bottom of the first heart engaging member of FIG. 3A.
Figure 4B:
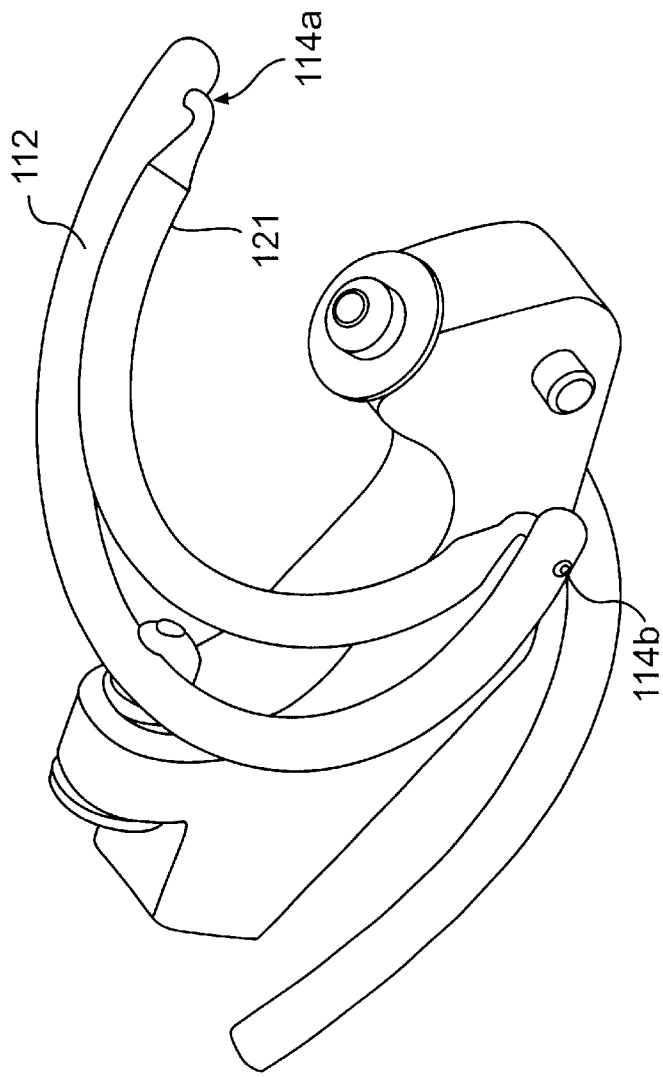
FIG. 4B is an isometric view of the apparatus of FIG. 4A without the heart engaging member.

As shown in FIG. 1, a first arm 110 is held in first arm receiving aperture 162a of bottom handle portion 152. First arm 110 is not movable with respect to bottom handle portion 152. First arm 110, at its end, supports a first heart engaging member 120, as shown in more detail in FIGS. 3A and 4A. Heart engaging member 120 is attached to arm 110 via pivot arm 112. Pivot arm 112 attaches to first arm 110 via clasp 116 (shown in greater detail in FIG. 3). Pivot arm 112 is rotatable with respect to first arm 110 about clasp 116. Pivot arm 112 attaches to heart engaging member 120 via two pivot pins 114a, 114b. Pivot pins 114a, 114b are attached to a semi-circular rail 121 which fits within a channel 121a formed on an outside wall of heart engaging member 120 (see FIGS. 3B and 4B). Pivot pins 114a, 114b move with semi-circular rail 121 in channel 121a the direction indicated by arrow 121b (FIGS. 3A and 4A). Thus, pivot arm 112 is rotatable with respect to heart engaging member 120. Heart engaging member 120 is articulable with respect to pivot arm 112 via pivot pins 114a, 114b.

First arm 110 also includes a guide 118 for receiving a guide tube 130. Guide tube 130 is intended to receive and guide a path-creating member, such as a needle, into and through the heart. Preferably, arm 110 and guide tube 130 are made from a material such as 316 stainless steel. First arm 110, pivot arm 112, and guide tube 130 are preferably hollow tubes. Arm 110 preferably includes a straight portion 110a and a curved portion 110b. Straight portion 110a is adjacent bottom handle portion 152. Curved portion 110b supports heart engaging member 120. The curve of curved portion 110b allows arm 110 to encircle a portion of the heart. Thus, a discussed below in more detail, when handle portions 152, 160 are mated, arms 110, 140 encircle the heart, attached to respective heart engaging members on either side of the heart.

The pivotable connections between pivot arm 112 and heart engaging member 120 and arm 110 allow heart engaging member 120 to articulate in any direction with respect to arm 110. The pivoting motion occurs around pivot pins 114a, 114b, clasp 116, and semi-circular rail 121. This allows heart engaging member 120 to articulate with respect to the heart to achieve and maintain contact with the surface of the heart, independent of movement of arm 110, particularly when suction is applied to heart engaging member 120, as will be described.

Heart engaging member 120 is preferably in the form of a circular or c-shaped cup, the bottom surface of which has a heart contacting surface and the outside wall of which includes a channel 121a to receive semi-circular rail 121. The end of guide tube 130 is positioned at the center of the heart engaging member 120. The assembly at the end of arm 110, including heart engaging member 120 and pivot arm 112, is configured so that any pivoting motion of the heart engaging member 120 relative to arm 110 maintains the end of the guide tube 130 at the center of member 120. The end of guide tube 130 does not pivot with the heart engaging member 120.

Rather, it is fixedly attached to the arm 110. In addition, a c-shape to the heart engaging member 120 is preferable to allow the heart contacting surface to be placed on the heart without disturbing (i.e., may be placed around) any markers in/on the heart.

The bottom heart contacting surface of the heart engaging member 120, as shown in FIG. 4, includes a plurality of suction chambers 122. Each chamber includes a suction inlet 124. Preferably, heart engaging member 120 is made of 15% glass filled nylon, however other suitable materials may be used. Heart engaging member 120 is connected to a vacuum source 135 via a vacuum line 132 and shutoff valve 134 to provide a vacuum to suction chambers 122. The vacuum applied at chambers 122 will ensure that a position of heart engaging member 120 on the heart is maintained securely. Heart engaging member 120 may have its own vacuum source or may share a vacuum source with other tools or parts of the alignment device. If the vacuum source 135 is shared, it is preferable that each item using the source have its own shutoff valve. Preferably, the vacuum source is approximately a 400 mm Hg vacuum (approximately ½ atmosphere). It has been observed that heart engaging member 120, when pressed to the heart's surface, remains firmly engaged with the surface, even in the absence of any vacuum applied.

By providing a plurality of suction chambers 122, it is possible to ensure that at least some of the chambers will establish secure contact with the heart's surface, which may be uneven, and a suction can therefore be applied and maintained at those chambers. It is also preferable that a vent be provided for the suction chambers 122 so that the suction can be eliminated when the vacuum source 135 is turned off. An exemplary vent may include a small bleeder hole at any point along the suction line.

This will also allow for easy release of the chambers from the heart surface and allow for repositioning of the heart engaging member 120 on the heart as necessary. The bleeder hole must be small enough that a strong vacuum can still be applied to the suction chambers 122 when the vacuum source is on.

Once the suction chambers 122 are secured to the heart via suction, the pivot pins 114a, 114b, clasp 116, and semi-circular rail 121 allow the arm 110 and bottom handle portion 152 to articulate in any direction with respect to the secured heart engaging member 120 without applying any disturbing force to member 120 that would force member 120 away from the heart. Thus, because arm 110 and bottom handle portion 152 may articulate with respect to the secured heart engaging member 120, movement of handle portion 152 will not cause dislodging or displacement of the heart engaging member 120 or cause undue trauma to the heart's surface.

Figure 5:
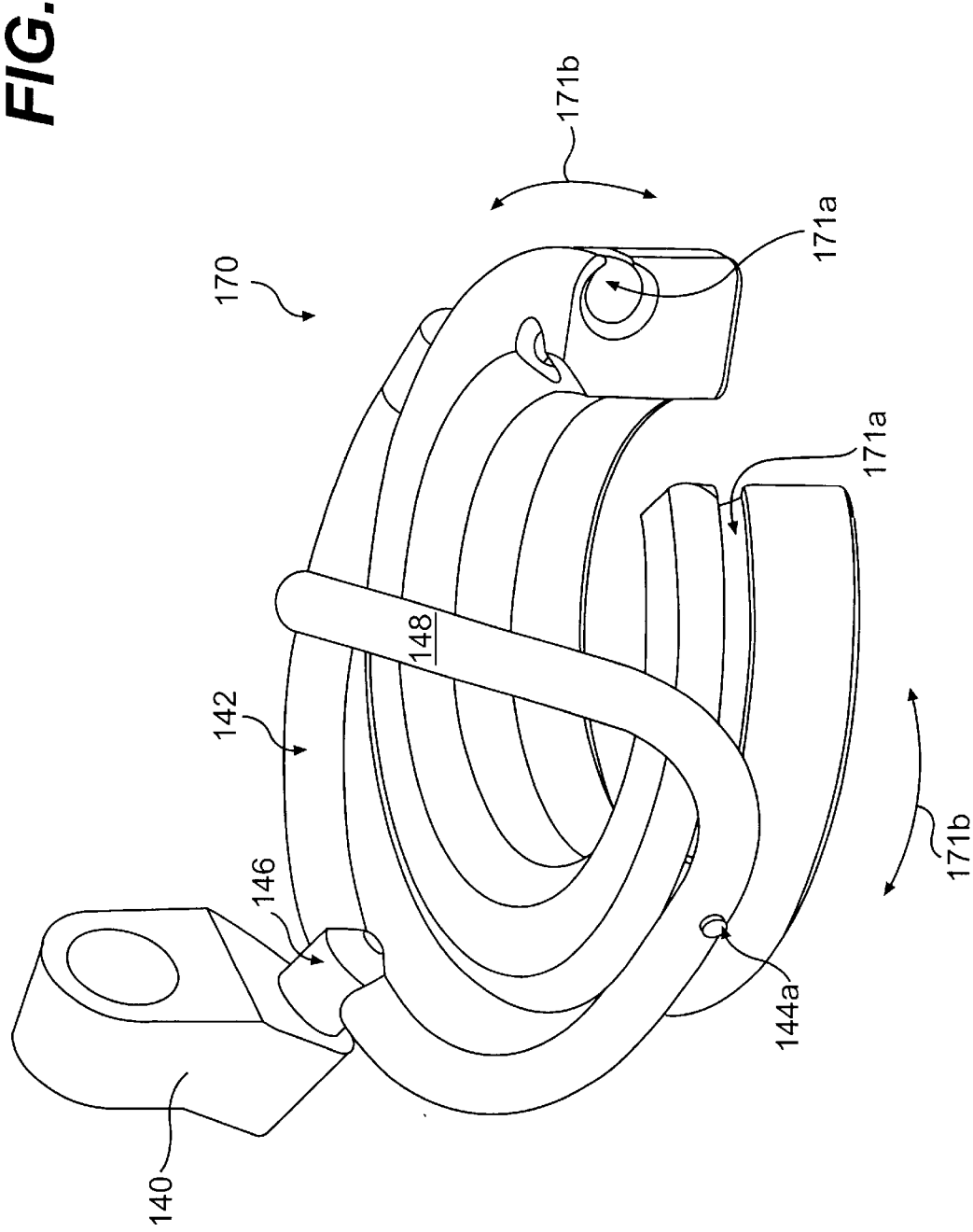
FIG. 5 is an isometric view of the top of a second heart engaging member of the alignment device of FIG. 1.
Figure 6:
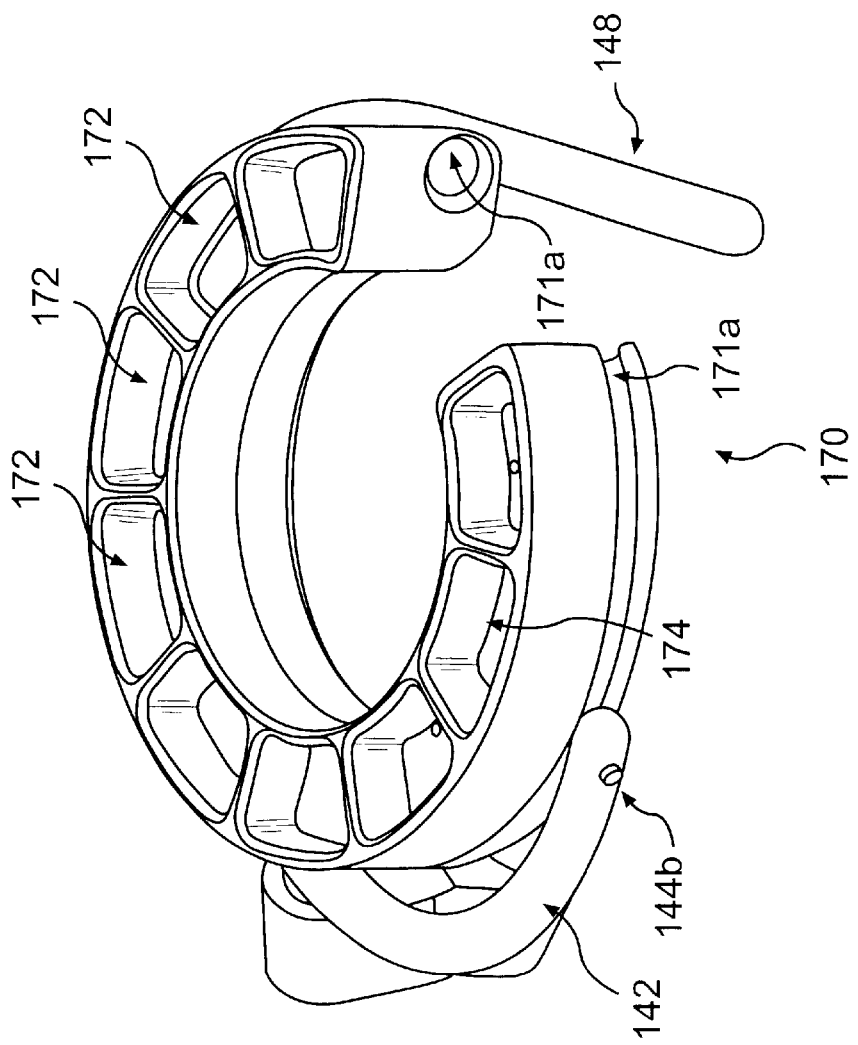
FIG. 6 is an isometric view of the bottom of the second heart engaging member of FIG. 5.

As shown in FIG. 1, a second arm 140 is held in second arm receiving aperture 162b of upper handle portion 160. Second arm 140 is not rotatable with respect to the handle assembly 150. Second arm 140 supports a second heart engaging member 170 at an end of arm 140. Heart engaging member 170, shown in detail in FIGS. 5 and 6, is attached to arm 140 via pivot arm 142. Pivot arm 142 attaches to second arm 140 via clasp 146. Pivot arm 142 is rotatable with respect to second arm 140 about clasp 146. Pivot arm 142 attaches to heart engaging member 170 via two pivot pins 144a, 144b. Pivot pins 144a, 144b are attached to a semi-circular rail 171 which fits within a channel 171a formed on an outside wall of heart engaging member 170 (similar to that shown in FIGS. 3B and 4B, and as shown in FIG. 5). Pivot pins 144a, 144b move with semi-circular rail 171 in channel 171a the direction indicated by arrow 171b (FIG. 5). Thus, pivot arm 142 is rotatable with respect to heart engaging member 170. Heart engaging member 170 is articulable with respect to pivot arm 142 about pivot pins 144a, 144b.

Second arm 140 and stop arm 148 are preferably hollow tubes or solid rods made of a material such as stainless steel. Other suitable materials may be used.

Arm 140 preferably includes a straight portion 140a and a curved portion 140b. Straight portion 140a is adjacent upper handle portion 160. Curved portion 140b supports heart engaging member 170. The curve of curved portion 140b allows arm 140 to encircle a portion of the heart. Thus, as discussed below in more detail, when handle portions 152, 160 are mated, arms 110, 140 encircle the heart, attached to respective heart engaging members 120, 170 on either side of the heart.

An end of pivot arm 142 supports a stop arm 148, which extends from arm 142. Arm 148 supports a needle stop 180 (shown in FIG. 1). Needle stop 180 is a circular plate with a sufficiently large surface area intended to prevent the passage of a path-creating member, such as a needle, beyond it. In use of the alignment device, a path-creating member, such as a needle or other sharp element, will be passed through the guide tube 130, through the center of rotation of heart engaging member 120, through a first heart wall and out a second heart wall, and through the center of rotation of heart engaging member 170. Needle stop 180 prevents the needle or sharp element from passing beyond the heart engaging element 170, and possibly damaging surrounding tissues. Needle stop 180 has a surface that faces the exiting needle that has an area approximately the same size as the diameter of the heart engaging member 170. Needle stop 180 also is concentric with the center of the heart engaging member 170 and rotates with member 170.

The pivotable connections between pivot arm 142 and heart engaging member 170 and arm 140 allow heart engaging member 170 to articulate in any direction with respect to arm 140. The pivoting motion occurs about pivot pins 144a, 144b, about clasp 146, and about semi-circular rail 171. This allows heart engaging member 170 to articulate with respect to the heart to achieve and maintain contact with the surface of the heart, independent of movement of arm 140, particularly when suction is applied to heart engaging member 170, as will be described.

Heart engaging member 170 is preferably in the form of a circular or c-shaped cup, the bottom surface of which has a heart contacting surface and the outside wall of which includes a channel 171a to receive semi-circular rail 171. The center of needle stop 180 is positioned at the center of the heart engaging member 170. The assembly at the end of arm 140, including heart engaging member 170 and arm 142 is configured so that any pivoting motion of the heart engaging member 170 relative to arm 140 maintains needle stop 180 in a position to engage a needle emerging from the center of the heart engaging member 170 no matter the angle that the needle sits at once the arms of the alignment device are connected.

The bottom heart contacting surface of the heart engaging member 170, as shown in FIG. 6, includes a plurality of suction chambers 172. Each chamber includes a suction inlet 174. Heart engaging member 170 is connected to a vacuum source 135 via a vacuum line 137 and shutoff valve 136 to provide a vacuum to suction chambers 172. By providing a plurality of suction chambers 172, it is possible to ensure that at least some of the chambers will establish secure contact with the heart's surface, which may be uneven, and a suction can therefore be applied and maintained at those chambers. It is also preferable that a vent be provided for the suction chambers 172, so that the suction can be eliminated when the vacuum source 135 is turned off. An exemplary vent may include a bleeder hole at any point along the suction line. This will also allow for easy release of the chambers from the heart surface and allow for repositioning of the heart engaging member 170 on the heart as necessary.

Once the suction chambers 172 are secured to the heart via suction, the pivot pins 144a, 144b, clasp 146, and semi-circular rail 171 allow the arm 140 and top handle portion 160 to articulate in any direction with respect to the secured heart engaging member 170 without applying any force to heart engaging member 170 that would force member 170 away from the heart. Thus, because arm 140 and top handle portion 160 may articulate with respect to the secured heart engaging member 170, movement of handle portion 160 will not cause dislodging or displacement of the heart engaging member 170 with respect to the heart's surface.

In one embodiment, as shown in FIG. 1, heart engaging members 120 and 170 share a vacuum source 135. In such an embodiment, it is preferable that each heart engaging member have its own cutoff valve 134, 136, respectively, for the vacuum source 135. This enhances the independence of each heart engaging member from the other, allowing each member to be independently placed and securely maintained relative to the heart.

Although described herein with respect to heart surgery, it is contemplated that alignment device 100 may be suitable for use in other surgical procedures, where a stable marking and/or alignment device is beneficial. Thus, the although the tissue engaging members 120, 170 of alignment device 100 have been characterized as heart engaging members, it is contemplated that they may be used to engage any type of tissue with their respective tissue contacting surfaces.

In use, after desired locations on the heart are determined (and marked if desired) as discussed previously, a surgeon will position heart engaging member 120 on the heart surface in one of the desired locations. While heart engaging member 120 is being positioned, bottom handle portion 152 which supports arm 110 is not locked to upper handle portion 160. Thus, arm 110 and heart engaging member 120 are movable independent of arm 140 and heart engaging member 170. This allows a surgeon to concentrate on positioning each heart engaging member at precisely the proper location, without interference from the other heart engaging member, were it to be already attached.

Because the heart engaging member 120 is articulatable with respect to the arm 110, it is possible to manipulate heart engaging member 120 to obtain secure contact between it and the heart's surface. Once the heart engaging member 120 is positioned as desired, the vacuum source 135 is activated, providing a vacuum to suction chambers 122. Member 120 then adheres to the heart's surface by the vacuum. Once heart engaging member 120 is secured to the heart's surface, it is possible to move arm 110 and handle portion 152 without dislodging the heart engaging member 120. First, the vacuum is strong enough to provide a strong seal between the heart's surface and the heart engaging member 120. Second, the arm 110 and handle portion 152 (which are not movable with respect to one another and thus move as a unit) are articulatable with respect to heart engaging member 120 via the assembly of the end of arm 110, including clasp 116, pivot pins 114a, 114b, and semi-circular rail 121.

After heart engaging member 120 is in contact with and adhering to the heart's surface, heart engaging member 170 is positioned in s similar fashion. While heart engaging member 170 is being positioned, upper handle portion 160 which supports arm 140 is not locked to bottom handle portion 152. Thus, arm 140 and heart engaging member 170 are movable independent of arm 110 and heart engaging member 120.

Because the heart engaging member 170 is articulatable with respect to the arm 140, it is possible to manipulate heart engaging member 170 to obtain secure contact between it and the heart's surface. Once the heart engaging member 170 is positioned as desired, the vacuum source 135 is activated, providing a vacuum to suction chambers 172. Member 170 then adheres to the heart's surface by the vacuum. Once heart engaging member 170 is secured to the heart's surface, it is possible to move arm 140 and handle portion 160 without dislodging the heart engaging member 170. First, the vacuum is strong enough to provide a strong seal between the heart's surface and the heart engaging member 170. Second, the arm 140 and handle portion 160 (which are not movable with respect to one another and thus move as a unit) are articulatable with respect to heart engaging member 170 via the assembly at the end of arm 140, including clasp 146, pivot pins 144a, 144b, and semicircular rail 171.

Once both heart engaging members 120, 170 are secured to the heart's surface, the arms 110, 140 can be moved closer together or farther apart by movement of the upper handle portion 160 with respect to the bottom portion 152. Movement of the arms and handles allows for trial shape changing of the heart to verify that appropriate positions on the heart have been chosen and marked. This trial method can be accompanied by suitable imaging. After both heart engaging members 120, 170 have been positioned and attached to the heart, upper handle portion 160 and bottom handle portion 152 are moved towards each other so that portion 160 is on top of portion 152. Portion 160a of upper handle portion 160 is pushed into trough portion 152a of lower handle portion 152 to permit portions 160 and 152 to be positioned together. Levers 158a, 158b then snap into place to lock together portions 160 and 152.

Once the arms 110, 140 and handle portions 160, 152 are locked in position, while the vacuum is on, a needle is passed through guide tube 130, through the center of rotation of the heart engaging member 120, into the heart. The needle exits the heart, passes through the center of rotation of the second heart engaging member 170, and runs into needle stop 180 which prevents the needle from moving further.

Once a path transverse to the heart has been made by passing the needle through the heart, the suction can be shut off and the alignment device removed from the heart. The splint assembly may be delivered and attached to the heart by any of various delivery techniques that have been described in prior applications, such as U.S. patent application Ser. No. 09/123,977, filed on Jul. 29, 1998, and entitled "Transventricular Implant Tools and Devices," and U.S. patent application Ser. No. 09/532,049, filed on Mar. 21, 2000, and entitled "A Splint Assembly for Improving Cardiac Function in Hearts, and Method for Implanting the Splinting Assembly," the entire disclosures of which are incorporated herein by reference.

Figure 7:
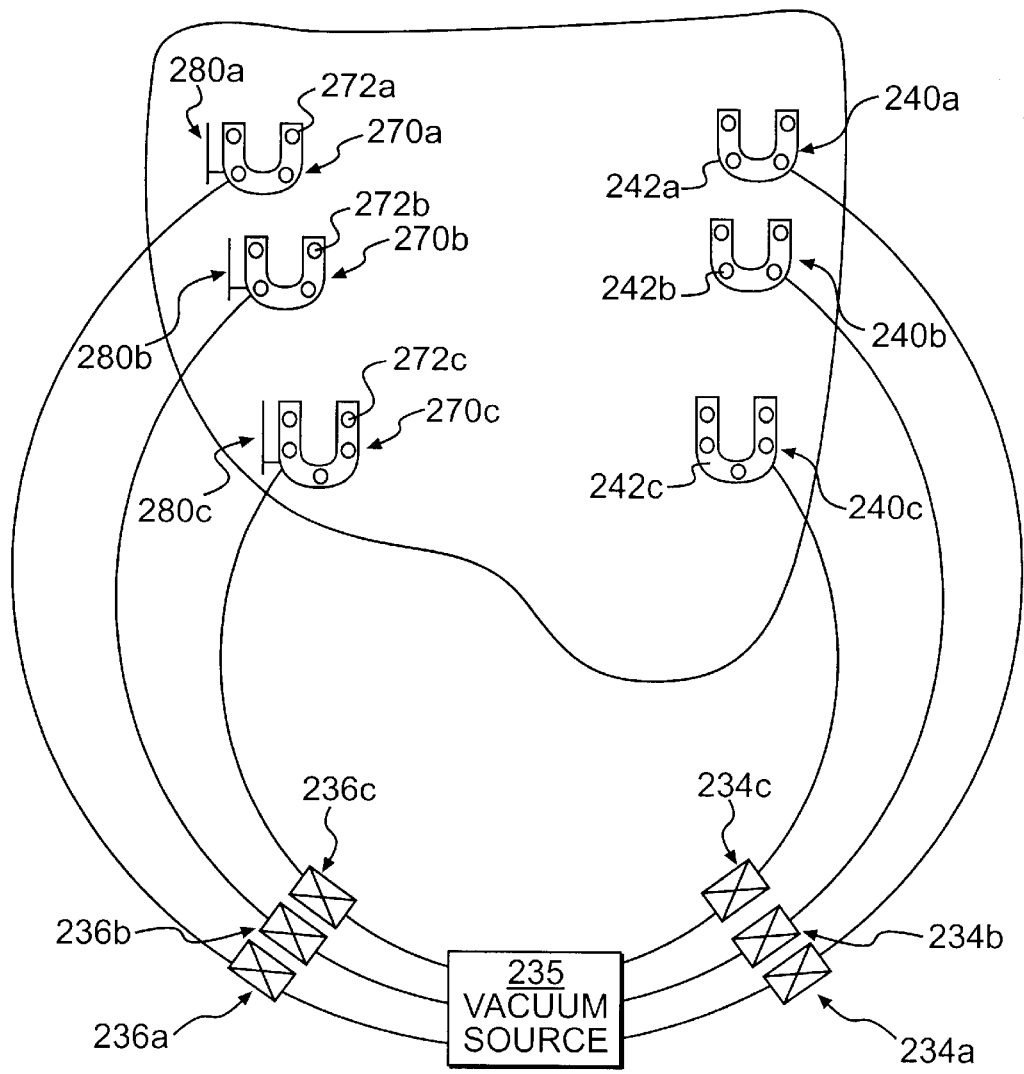
FIG. 7 is a top view of heart engaging members used as a locating and marking device according to an embodiment of the present invention.

According to another aspect of the present invention, the heart engaging members need not be permanently attached to the arms of the alignment device. As embodied herein and shown in FIGS. 7–10, the heart engaging members may be provided separately from the alignment device 200. In such an embodiment, the heart engaging members may be used as marking devices. As shown in FIG. 7, first heart engaging members 220a, 220b, and 220c having suction chambers 222a, 222b, and 222c, respectively, are positioned on the heart to indicate the location of the desired placement of the tension members of the splint assemblies through the heart. Once each heart engaging member 220a, 220b, 220c is positioned as desired, a vacuum source is activated and the corresponding valve 234a, 234b, 234c is opened to create suction within the chambers 222a, 222b, 222c, locking the heart engaging members onto the heart surface. Similarly, second heart engaging members 270a, 270b, and 270c having corresponding needle stops 280a, 280b, 280c and suction chambers 272a, 272b, and 272c, respectively, are positioned on the heart to indicate the location of the desired placement of the tension members of the splint assemblies through the heart. Once each heart engaging member 270a, 270b, 270c is positioned as desired, the vacuum source is activated and the corresponding valve 236a, 236b, 236c is opened to create suction within the chambers 272a, 272b, 272c, locking the heart engaging members onto the heart surface and marking the areas through which the needle should pass through the heart.

Figure 8:
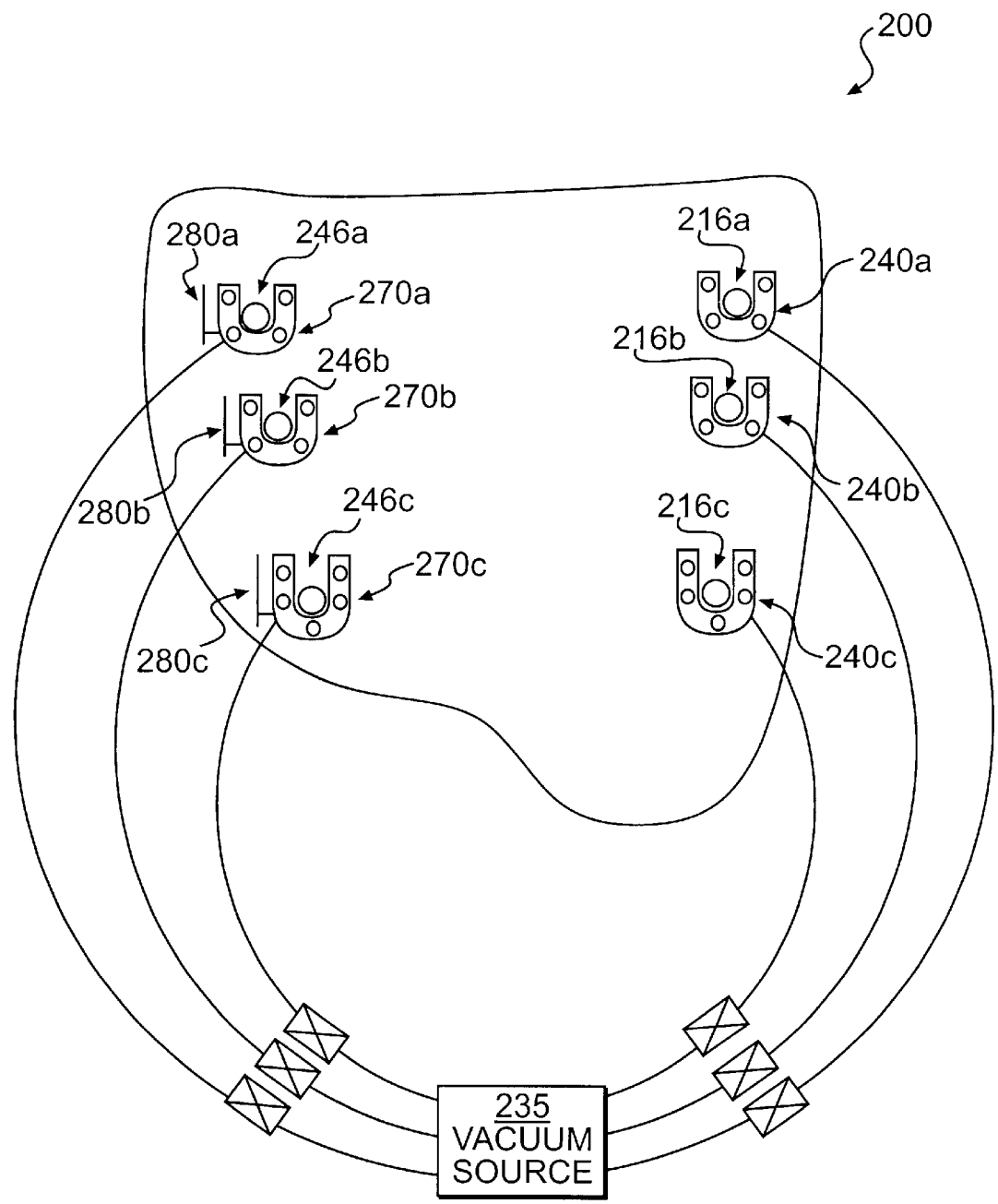
FIG. 8 is a top view of the heart engaging members of FIG. 7 attached to ball joints of the alignment device.
Figure 9:
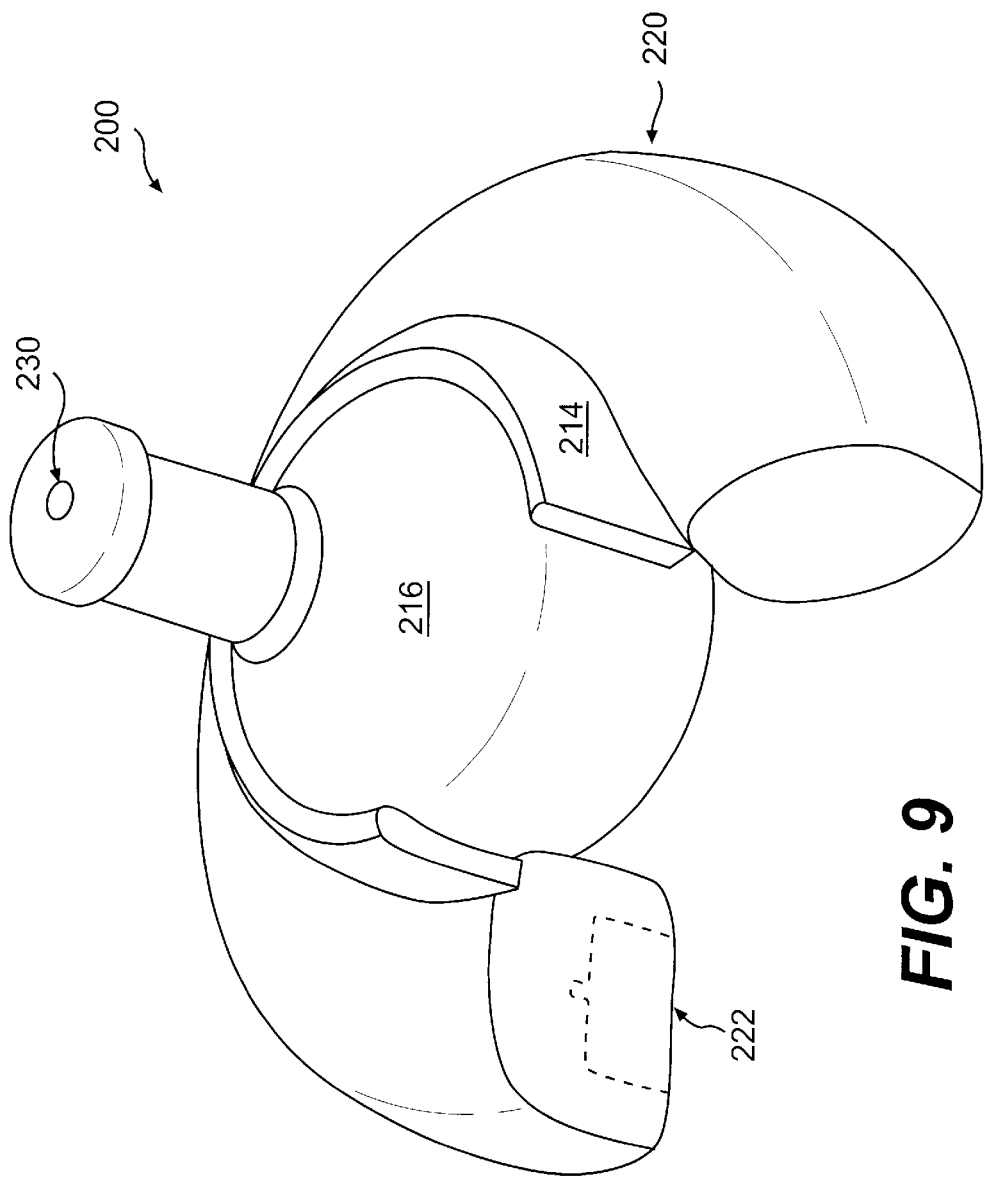
FIG. 9 is an isometric view of a first heart engaging member attached to a ball joint via a socket according to an embodiment of the invention.
Figure 10:
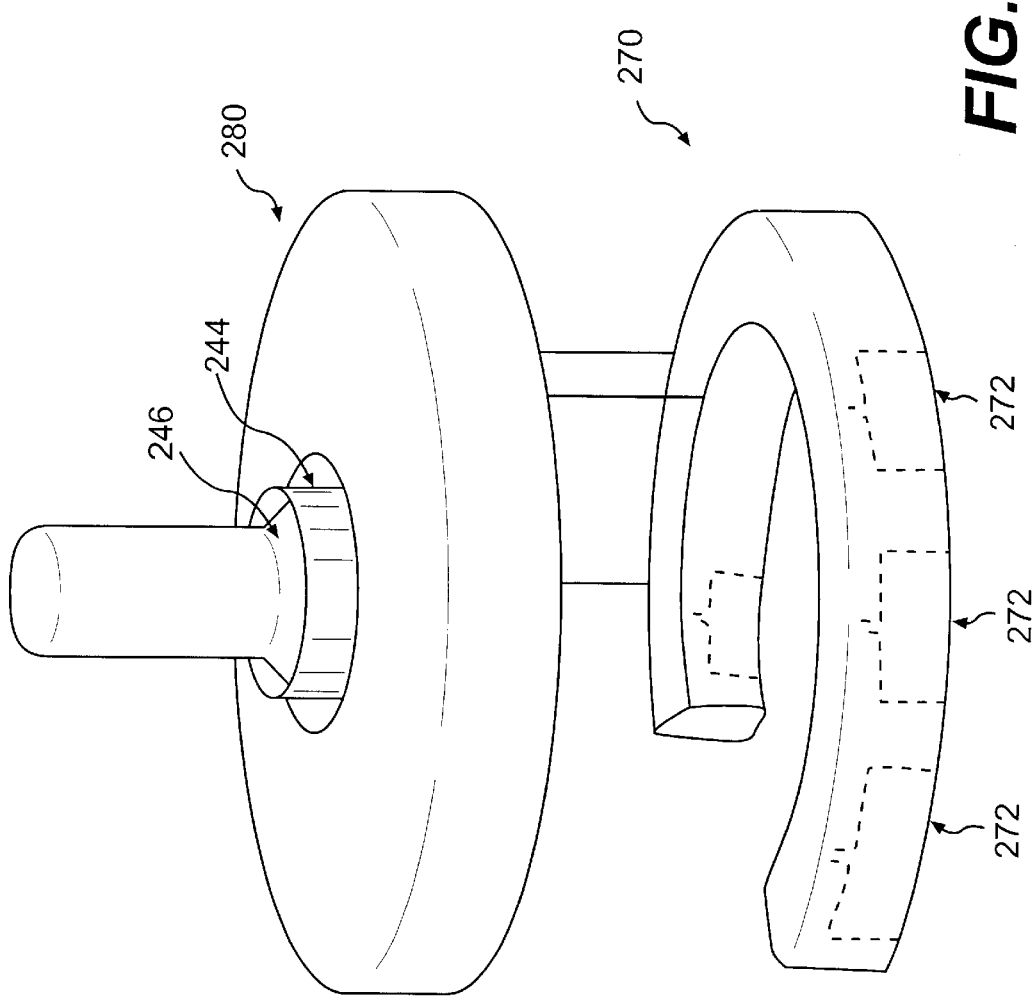
FIG. 10 is an isometric view of a second heart engaging member attached to a ball joint via a socket according to an embodiment of the invention.

As shown in FIG. 8, after the heart engaging members are attached to the heart to mark the desired locations, the alignment device is connected to a pair of the heart engaging members 220a, 270a; 220b, 270b; 220c, 270c, preferably one pair at a time. As shown in FIG. 9, each first c-shaped heart engaging member 220 according to this embodiment may include a socket portion 214 for receiving a ball joint 216 permanently attached to the arm 210 of the alignment device. The first heart engaging member 220, will attach to a ball joint 216 having a portion through which a guide tube 230 passes. As shown in FIG. 10, each second c-shaped heart engaging member 270 according to this embodiment may include a socket portion 244 for receiving a ball joint 246 permanently attached to the arm 240 of the alignment device. Thus, once the ball joint 216 is snapped into the socket 214, a path-creating member, such as a needle, can be passed through the guide tube 230 into the heart, out of the heart, through the ball joint 246 connected to socket 244 of the second heart engaging member 270, and into the needle stop 280. Other than attaching the heart engaging members and then inserting the ball joint into the socket of the heart engaging members to attach the alignment device, the method of use is the same as described previously with respect to the embodiment of the alignment device shown in FIGS. 1–6.

Although described herein with respect to heart surgery, it is contemplated that alignment device 200 may be suitable for use in other surgical procedures, where a stable marking and/or alignment device is beneficial. Thus, the although the tissue engaging members 220, 270 of alignment device 200 have been characterized as heart engaging members, it is contemplated that they may be used to engage any type of tissue with their respective tissue contacting surfaces.

According to another aspect of the present invention, the heart engaging members may be applied to the heart's surface to facilitate a minimally invasive procedure such as a splint implantation. The alignment device described in the two previous embodiments is adapted for more invasive procedures, such as open heart surgery. A minimally invasive procedure, such as implantation of a splint device, is disclosed in related U.S. patent application Ser. No. 09/123, 977 entitled "Transventricular Implant Tools and Devices," filed Jul. 29, 1998, the complete disclosure of which is incorporated herein by reference. In such a less invasive method, access to the heart is achieved through at least two oppositely disposed lateral ports in the chest wall. U.S. patent application Ser. No. 09/123,977 describes several methods for delivery of a splint through the use of one or more access points in the chest.

Figure 11:
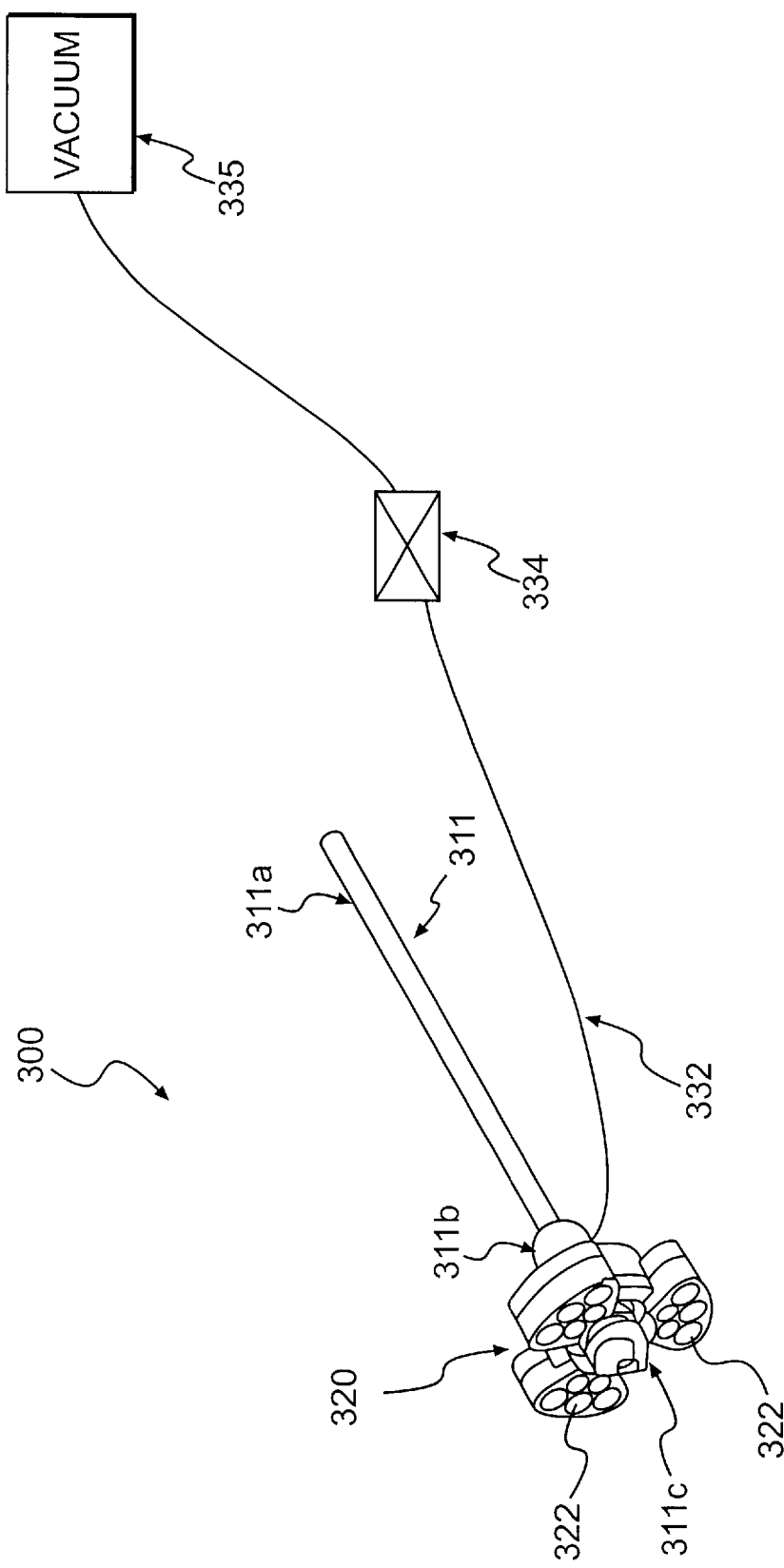
FIG. 11 is an isometric view of a heart engaging member and probe according to another embodiment of the invention.

As embodied herein and shown in FIG. 11, an alignment device 300 is provided. The alignment device 300 is designed such that it can be used to secure and/or mark a location on the heart, and particularly serve as a delivery conduit for facilitating a minimally invasive delivery of a splint. Alignment device 300 includes a heart engaging member having a heart contact surface and may further include an advanceable probe. For delivery of a splint, two alignment devices 300 would preferably be utilized, each one introduced through a separate, small incision in the chest wall corresponding to the general final position of each anchor pad used to anchor the tension member.

Figure 12A:
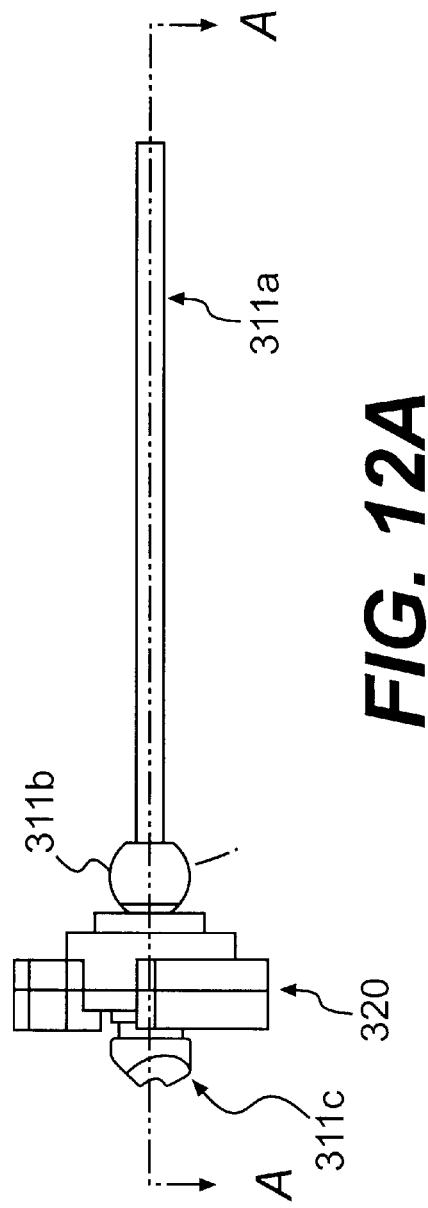
FIG. 12A is a side view of the heart engaging member and probe of FIG. 11.
Figure 12B:
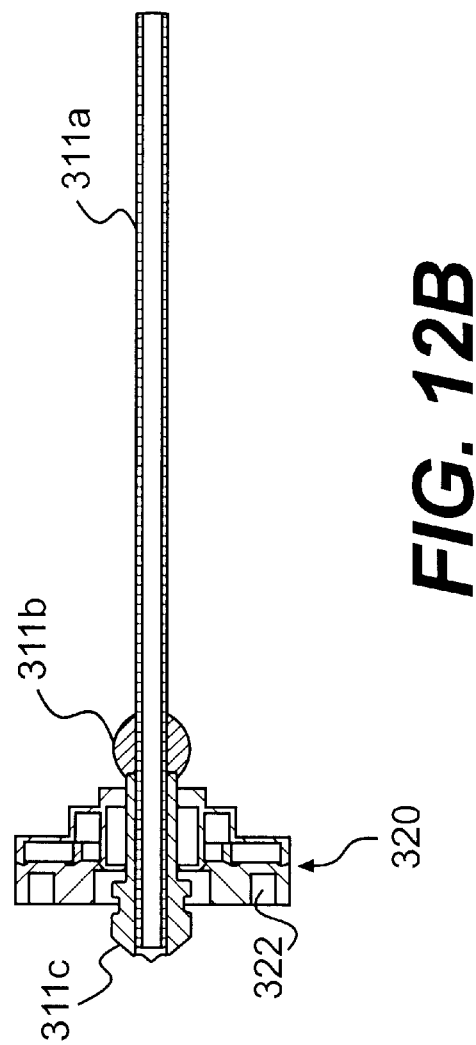
FIG. 12B is a cross-sectional side view of the heart engaging member and probe taken along line A—A of FIG. 12A.

As shown in FIGS. 11 and 12, an advanceable probe 311 is provided. Probe 311 includes a hollow shaft portion 311a, a grasper portion 311b, and surface contacting portion 311c. The hollow shaft portion 311a forms a lumen for receiving and passing catheters, wires, needles, snares, and any other surgical devices through to a desired position on the heart's surface. Additionally, the lumen of hollow shaft portion 311a may be used to pass a tension member through to the heart. Grasper portion 311b is configured to be engaged by a grasper used to move the probe within the body (see FIG. 13). Preferably, grasper portion 311b is in the form of a ball, however, other suitable shapes may be used. The surface contacting portion 311c of the probe 311 includes an exit for the lumen formed by hollow shaft 311a. Surface contacting portion 311c is configured to maintain a heart engaging member on the probe 311. Thus, it is preferable that the surface contacting portion 311c of the probe 311 is larger than a lumen in the heart engaging member through which the probe passes to support the heart engaging member. Advanceable probe 311 is preferably made from any suitable metal or polymer.

Advanceable probe 311 supports a heart engaging member 320. Advanceable probe 311 is movable independent of heart engaging member 320. Heart engaging member 320 includes a lumen through which the shaft portion 311a of probe 311 can pass. Heart engaging member 320 is maintained on probe 311 between the grasper portion 311b and the surface contacting portion 311c of the probe 311. As shown in FIG. 11, heart engaging member 320 preferably has a clover or three-leaf shape. However, other shapes, such as circular, oval, star-shaped, etc., may be suitable. Preferably, heart engaging member 320 is made of 15% glass filled nylon, however other suitable materials such as silicone and polyurethane may be used.

Heart engaging member 320 includes a heart contacting surface having at least one suction chamber 322, and preferably including a plurality of suction chambers 322. Each chamber includes a suction inlet. Heart engaging member 320 is connected to a vacuum source 335 via a vacuum line 332 and shutoff valve 334 to provide a vacuum to suction chambers 322. The vacuum applied at chambers 322 will ensure that a position of heart engaging member 320 on the heart is maintained securely. Heart engaging member 320 may have its own vacuum source or may share a vacuum source with other tools or parts of the alignment device. If the vacuum source 335 is shared, it is preferable that each item using the source have its own shutoff valve. Preferably, the vacuum source is approximately a 400 mm Hg vacuum (approximately ½ atmosphere).

By providing a plurality of suction chambers 322, it is possible to ensure that at least some of the chambers will establish secure contact with the heart's surface, which may be uneven, and a suction can therefore be applied and maintained at those chambers. It is also preferable that a vent be provided for the suction chambers 322 so that the suction can be eliminated when the vacuum source 335 is turned off. An exemplary vent may include a small bleeder hole at any point along the suction line. This will also allow for easy release of the chambers from the heart surface and allow for repositioning of the heart engaging member 320 on the heart as necessary. The bleeder hole must be small enough that a strong vacuum can still be applied to the suction chambers 322 when the vacuum source is on.

Figure 13:
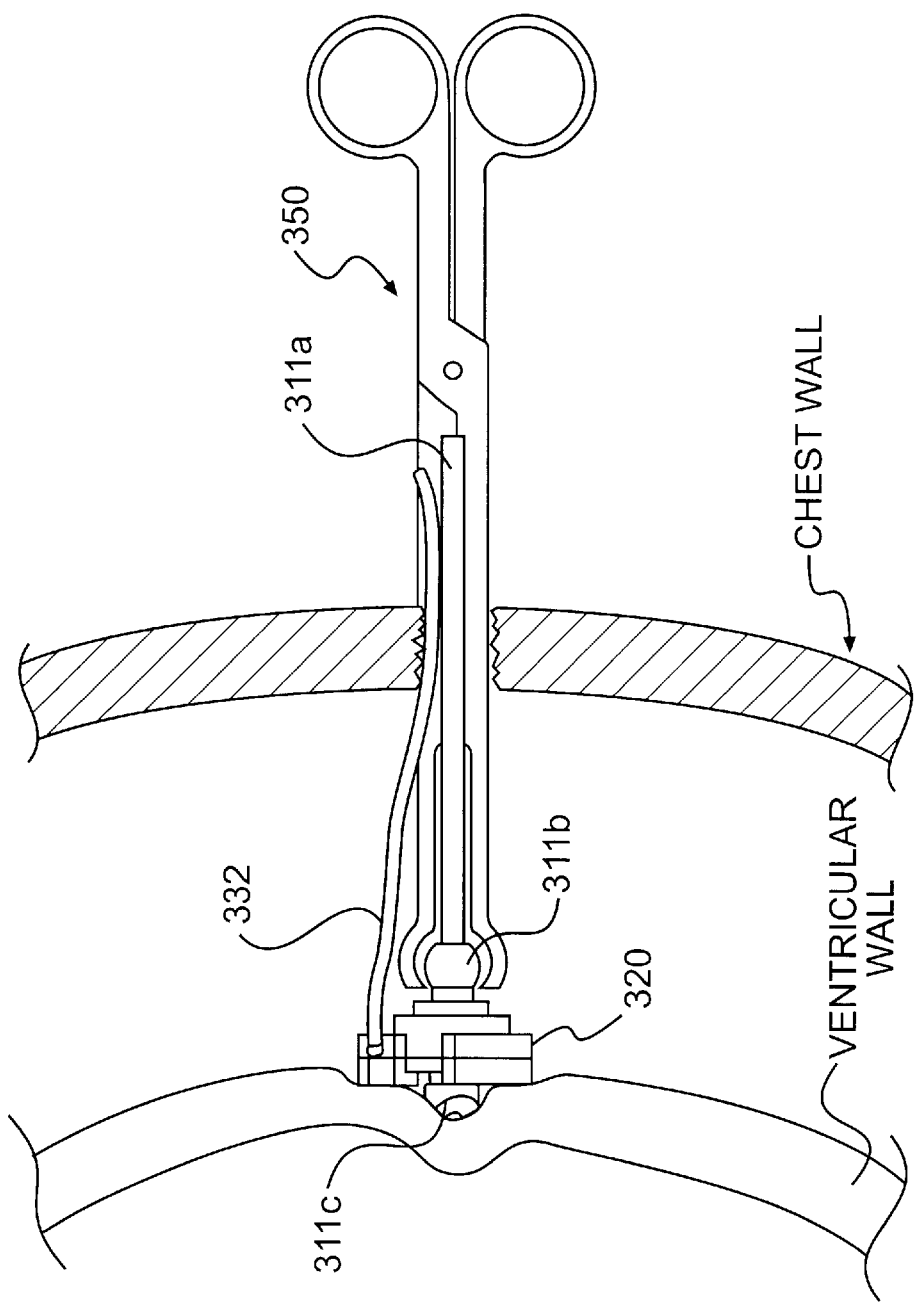
FIG. 13 is a side view of the heart engaging member and probe of FIG. 11 engaging an outer surface of the heart during use.

Prior to use of the device 300, an access port is created in the chest cavity at a location near the desired location for surface implantation of the tension member (see FIG. 13). In the case of a splint implantation, a second device 300 is positioned through a different access port, in association with a different heart wall location. The alignment device 300 is introduced through the chest wall to a position on the ventricular surface of the heart. Once near or one the heart wall, the vacuum source 335 is turned on, valve 334 opened, and suction applied to suction chambers 322 of heart engaging member 320 via suction line 332. The suction secures the suction chambers 322 of heart engaging member 320 to the surface of the heart.

Once the heart engaging member 320 is positioned on the heart, it is possible to verify whether the positioning of the heart engaging member is desirable. A grasper 350 is introduced through the chest wall and grasps the probe by grasping the grasping portion 311b of the probe 311. Grasper 350 is then used to advance probe 311 toward the heart in a direction perpendicular to the heart wall. Because probe 311 is not connected or attached to heart engaging member 320, the heart engaging member does not move with the probe when attached to the heart. As probe 311 moves toward the heart, surface contacting portion 311c of probe 311 engages the heart wall and creates a local indentation in the heart wall. This indentation, together with probe 311, is visible using appropriate imaging techniques, such as transesophageal echo (TEE), and can be compared to internal structures in the heart, such as the papillary muscles or valve chordae to determine if positioning of the heart engaging member 320 is correct.

If the position of the heart engaging member 320 is correct, then various catheters, wires, needles, snares, or other appropriate surgical devices such as those described in U.S. patent application Ser. No. 09/123,977 can be delivered through the lumen of shaft 311a of the device(s) 300 to facilitate delivery of a splint. If the position is not correct, the vacuum is released, the heart engaging member 320 is withdrawn from the wall of the heart and is re-positioned before the vacuum is again applied. The desirability of the new position will then be assessed prior to commencing the surgical implantation of the tension member. Although described herein with respect to heart surgery, it is contemplated that device 300 may be suitable for use in other minimally invasive procedures, where a stable marking and/or alignment device is beneficial.

Thus, the although the tissue engaging member 320 of alignment device 300 has been characterized as a heart engaging member, it is contemplated that it may be used to engage any type of tissue with its tissue contacting surface.

It will be understood that this disclosure, in many respects, is only illustrative. Changes may be made in details, particularly in matters of shape, size, material, number and arrangement of parts without exceeding the scope of the invention. Accordingly, the scope of the invention is as defined in the language of the appended claims. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method of implanting an elongate member transverse a heart, comprising:

selecting first and second locations on the heart;

placing a first heart engaging member at the first location;

placing a second heart engaging member at the second location while the second heart engaging member is not connected to the first heart engaging member;

passing a path-creating member through the first and second heart engaging members and through the heart; and placing an elongate member through the heart along a path created by the path creating member.

2. The method of claim 1, further including securing the first heart engaging member to the first location via suction.

3. The method of claim 2, further including securing the second heart engaging member to the second location via suction.

4. The method of claim 1, further including connecting a first arm connected to the first heart engaging member with a second arm connected to the second heart engaging member.

5. The method of claim 4, wherein the connecting includes connecting a first handle portion supporting the first arm to a second handle portion supporting the second arm.

6. The method of claim 1, further including articulating a first arm relative to the first heart engaging member.

7. The method of claim 6, further including articulating a second arm relative to the second heart engaging member.

8. The method of claim 7, further including connecting the first and second arms via a handle assembly.

* * * * *